US008501167B2

(12) United States Patent
Apelian et al.

(10) Patent No.: US 8,501,167 B2
(45) Date of Patent: Aug. 6, 2013

(54) COMPOSITIONS AND METHODS FOR TARGETED ABLATION OF MUTATIONAL ESCAPE OF TARGETED THERAPIES FOR CANCER

(75) Inventors: David Apelian, Boonton Township, NJ (US); Alex Franzusoff, Denver, CO (US); Timothy C. Rodell, Aspen, CO (US)

(73) Assignee: GlobeImmune, Inc., Louisville, CO (US)

( * ) Notice: Subject to any disclaimer, the term of this patent is extended or adjusted under 35 U.S.C. 154(b) by 617 days.

(21) Appl. No.: 12/531,876

(22) PCT Filed: Jan. 17, 2008

(86) PCT No.: PCT/US2008/051348
§ 371 (c)(1), (2), (4) Date: Jan. 5, 2010

(87) PCT Pub. No.: WO2008/115610
PCT Pub. Date: Sep. 25, 2008

(65) Prior Publication Data
US 2010/0111912 A1 May 6, 2010

Related U.S. Application Data

(60) Provisional application No. 60/895,689, filed on Mar. 19, 2007, provisional application No. 60/910,796, filed on Apr. 9, 2007.

(51) Int. Cl.
| | | |
|---|---|---|
| A61K 39/00 | (2006.01) | |
| A61K 31/131 | (2006.01) | |
| A61K 31/136 | (2006.01) | |
| A61K 31/166 | (2006.01) | |
| A61K 31/167 | (2006.01) | |

(52) U.S. Cl.
USPC .................. 424/93.21; 424/93.51; 424/185.1; 424/192.1; 424/277.1; 514/257; 514/275; 514/279; 514/280; 514/577; 514/579; 514/617

(58) Field of Classification Search
None
See application file for complete search history.

(56) References Cited

U.S. PATENT DOCUMENTS

| | | | |
|---|---|---|---|
| 4,775,622 A | 10/1988 | Hitzeman et al. | |
| 5,234,830 A | 8/1993 | Oshima et al. | |
| 5,310,654 A | 5/1994 | Isberg et al. | |
| 5,413,914 A | 5/1995 | Franzusoff | |
| 5,676,950 A | 10/1997 | Small, Jr. et al. | |
| 5,731,182 A | 3/1998 | Boyce | |
| 5,786,211 A | 7/1998 | Johnson | |
| 5,830,463 A | 11/1998 | Duke et al. | |
| 5,858,378 A | 1/1999 | Bostwick | |
| 5,871,982 A | 2/1999 | Wilson et al. | |
| 5,919,651 A | 7/1999 | Hitzeman et al. | |
| 6,107,457 A | 8/2000 | Arlinghaus et al. | |
| 6,258,595 B1 | 7/2001 | Gao et al. | |
| 6,482,407 B2 | 11/2002 | Soo Hoo | |
| 6,759,046 B1 | 7/2004 | Gaudernack et al. | |
| 7,083,787 B2 | 8/2006 | Duke et al. | |
| 7,439,042 B2 | 10/2008 | Duke et al. | |
| 7,465,454 B2 | 12/2008 | Franzusoff et al. | |
| 7,563,447 B2 | 7/2009 | Franzusoff et al. | |
| 7,595,060 B2 | 9/2009 | Duke et al. | |
| 7,625,569 B2 | 12/2009 | Duke et al. | |
| 7,632,511 B2 | 12/2009 | Duke et al. | |
| 7,736,642 B2 | 6/2010 | Duke et al. | |
| 7,745,128 B2 | 6/2010 | Guo et al. | |
| 8,007,816 B2 | 8/2011 | Duke et al. | |
| 2002/0044948 A1 | 4/2002 | Khleif et al. | |
| 2003/0035810 A1 | 2/2003 | Caplan | |
| 2005/0074463 A1 | 4/2005 | Autran et al. | |
| 2007/0172503 A1 | 7/2007 | Selitrennikoff et al. | |
| 2009/0098154 A1 | 4/2009 | Franzusoff et al. | |
| 2009/0142366 A1 | 6/2009 | Franzusoff et al. | |
| 2009/0142367 A1 | 6/2009 | Franzusoff et al. | |
| 2009/0304741 A1 | 12/2009 | Duke et al. | |
| 2010/0034840 A1 | 2/2010 | Apelian et al. | |
| 2010/0104604 A1 | 4/2010 | Selitrennikoff et al. | |
| 2010/0150963 A1 | 6/2010 | Duke et al. | |
| 2010/0189749 A1 | 7/2010 | Franzusoff et al. | |
| 2010/0196411 A1 | 8/2010 | Duke et al. | |
| 2010/0215678 A1 | 8/2010 | Guo et al. | |
| 2011/0150909 A1 | 6/2011 | Franzusoff et al. | |

FOREIGN PATENT DOCUMENTS

| | | |
|---|---|---|
| EP | 0414404 | 2/1991 |
| EP | 1403283 | 3/2004 |
| FR | 2486400 | 1/1982 |
| WO | WO 96/02555 | 2/1996 |
| WO | WO 96/14876 | 5/1996 |
| WO | WO 02/39951 | 5/2002 |
| WO | WO 2004/058157 | 7/2004 |

(Continued)

OTHER PUBLICATIONS

Yan et al (Expert Opinion on Biological Therapy, 2005, vol. 5, pp. 691-702).*
Singh and Paterson (Cancer Research, 2007, vol. 67, pp. 1887-1892).*
Bocchia et al (The Lancet, 2005, vol. 365, pp. 657-662).*
Savage and Antman (New England Journal of Medicine, 2002; vol. 346, pp. 683-693).*
Burmeister et al, Leukemia, 2000, vol. 14, pp. 1850-1856.*
Dictionary of Biochemistry (3rd Edition), Tokyokagakudojin Co., Ltd., 1998, p. 1423.
Bui et al. "Mutation-specific control of BCR-ABL T315I positive leukemia with recombinant yeast-based therapeutic vaccine in a murine model." Vaccine, Aug. 23, 2010, vol. 28, No. 37, pp. 6028-6035.

(Continued)

*Primary Examiner* — Karen Canella
(74) *Attorney, Agent, or Firm* — Angela Dallas Sebor; Sheridan Ross P.C.

(57) ABSTRACT

Provided herein are compositions and methods for targeted ablation of mutational escape in the face of cancer therapeutic agents. Compositions comprising the yeast-based vehicles are used in combination with other cancer therapeutic agents.

20 Claims, 5 Drawing Sheets

FOREIGN PATENT DOCUMENTS

| | | |
|---|---|---|
| WO | WO 2010/033841 | 3/2010 |
| WO | WO 2010/065626 | 6/2010 |
| WO | WO 2010/121180 | 10/2010 |
| WO | WO 2011/032119 | 3/2011 |
| WO | WO 2011/115914 | 9/2011 |

OTHER PUBLICATIONS

Nazarian et al. "Melanomas acquire resistance to B-RAF(V600E) inhibition by RTK or N-RAS upregulation." NATURE, Dec. 16, 2010, vol. 468, pp. 973-979.

English translation of Official Action for China Patent Application No. 200880016530.8, issued Sep. 26, 2011 7 pages.

Examination Report for European Patent Application No. 06786760.6, dated Oct. 25, 2011 10 pages.

English translation of Israel Patent Application No. 201039, dated Oct. 31, 2011 3 pages.

English Translation of Israel Patent Application No. 188717, dated Dec. 6, 2011 2 pages.

English translation of Japan Patent Application No. 2008-521492, dated Dec. 6, 2011 6 pages.

English translation of Russia Patent Application No. 2009138327, dated Dec. 9, 2011 11 pages.

Ahmad, A.L.M. et al. (1987). "Studies of Rhinovirus Resistant to Antiviral Chalcone," Antiviral Res. 8:27-39.

Azam, M. et al. (e-pub. Oct. 24, 2003). "A Screen to Identify Drug Resistant Variants to Target-Directed Anti-Cancer Agents," Biol. Proced. Online 5(1):204-210.

Azam, M. et al. (Mar. 21,2003). "Mechanisms of Autoinhibition and STI-571/Imatinib Resistance Revealed by Mutagenesis of BCR-ABL," Cell 112:831-843.

Bett, A.J. et al. (Oct. 1993). "Packaging Capacity and Stability of Human Adenovirus Type 5 Vectors," J. Virol. 67(10):5911-5921.

Blencke, S. et al. (May 2004). "Characterization of a Conserved Structural Determinant Controlling Protein Kinase Sensitivity to Selective Inhibitors," Chem. Biol. 11:691-701.

Branford, S. et al. (May 1, 2002). "High Frequency of Point Mutations Clustered within the Adenosine Triphosphate-Binding Region of BCR/ABL in Patients with Chronic Myeloid Leukemia or Ph-Positive Acute Lymphoblastic Leukemia Who Develop Imatinib (STI571) Resistance," Blood 99(9):3742-3745.

Burgess, M.R. et al. (Aug. 11, 2006). "Treating Imatinib-Resistant Leukemia: The Next Generation Targeted Therapies," The Scientific World Journal 6:918-930.

Bussey, H. et al. (May 17, 1979). "Yeast Plasma Membrane Ghosts. An Analysis of Proteins by two-Dimensional gel Electrophoresis," Biochim. Biophys. Acta 553(2): 185-196, Abstract Only.

Capdeville, R. et al. (Jul. 2002). "Glivec (STI571, Imatinib), A Rationally Developed, Targeted Anticancer Drug," Nature Reviews 1:493-502.

Caux, C. et al. (Aug. 1, 1996). "CD43+ Hematopoietic Progenitors from Human Cord Blood Differentiate Along Two Independent Dendritic Cell Pathways in Response to GM-CSF+TNFa," J. Exp. Med. 184:695-706.

Coffin, J.M. (Jan. 27, 1995). "HIV Population Dynamics in Vivo: Implications for Genetic Variation, Pathogenesis, and Therapy," Science 267:483-489.

Cools, J. et al. (Mar. 27, 2003). "A Tyrosine Kinase Created by Fusion of the PDGFRA andFIP1L1 Genes as a Therapeutic Target of Imatinib in Idopathic Hpereosinophilic Syndrome," New Engl. J. Med. 348(13):1201-1214.

Cools, J. et al. (Sep. 15, 2004). "Prediction of Resistance to Small Molecule FLT3 Inhibitors: Implications for Molecularly Targeted Therapy of Acute Leukemia," Cancer Researc,h 64:6385-6389.

Coon, H.G. (May 1978). "The Genetics of the Mitochondrial DNA of Mammalian Somatic Cells, Their Hybrids and Cybrids," Natl. Cancer Inst. Monogr. 48:45-55, Abstract Only.

Deininger, M. et al. (Apr. 1, 2005). "The Development of Imatinib as a Therapeutic Agent for Chronic Myeloid Leukemia," Blood 105(7):2640-2653.

Doe, B. et al. (1994). "Induction of HIV-1 Envelope (gp120)-Specific Cytoxic T Lymphocyte Responses in Mice by Recombinant CHO Cell-Derived gp120 is Enhanced by Enzymatic Removal of N-Linked Glycans," Eur. J. Immunol. 24:2369-2376.

Duan, D. et al. (Dec. 1999). "Dynamin is Required for Recombinant Adeno-Associated Virus Type 2 Infection," J. Virol. 73(12):10371-10376.

Duan, D. et al. (Nov. 1998). "Circular Intermediates of Recombinant Adeno-Associated Virus Have Defined Structural Characteristics Responsible for Long-Term Episomal Persistence in Muscle Tissue," J. Virol. 72(11)8568-8577.

Erickson, A.L. et al. (Oct. 15, 1993). "Hepatitis C Virus-Specific CTL Responses in the Liver of Chimpanzees with Acute and Chronic Hepatitis C," J. Immunol., 151 (8):4189-4199.

Eyers, PA et al. (Jun. 3, 1998). "Conversion of SB 203580-Insensitive MAP Kinase Family Members to Drug-Sensitive Forms by a Single Amino-Acid Substitution," Chem. Bili. 5(6):321-328.

Franzusoff, A. et al. (1991). "Analysis of Polypeptide Transit Through Yeast Secretory Pathway," Meth. Enzymiol. 194:662-674.

Franzusoff, A. et al. (Apr. 1, 2005). "Yeasts Encoding Tumour Antigens in Cancer Immunotherapy," Expert Opinion on Biological Therapy 5(4):565-575.

Franzusoff, A.J. et al. (Mar. 25, 1983). "Glucose Transport Activity in Isolated Plasma Membrane Vesicles from *Saccharomyces cerevisiae*," J. Biol. Chem. 258(6):3608-3614.

Garcia-Quintanilla, A (Nov. 22,2007). "Overcoming Viral Escape with Vaccines that Generate and Display Antigen Diversity In Vivo," Virology Journal 4:125.

Gorre, M.E. et al. (Aug. 3, 2001, e-pub. Jun. 21, 2001). "Clinical Resistance to STI-571 Cancer Therapy Caused by BCR-ABL Gene Mutation or Amplification," Science 293:876-880.

Guthrie, C. et al. eds. (1991). Guide to Yeast Genetics and Molecular Biology, Academic Press: San Diego, CA, 194:v-ix, (Table of Contents Only.).

Haj-Ahmad, H. et al. (Jan. 1986). "Development of a Helper-Independent Human Adenovirus Vector and Its Use in the Transfer of the Herpes Simplex Virus Thymidine Kinase Gene," J. Virol. 57(1):267-274.

Holland, J.J. et al. (1992). "RNA Virus Populations as Quasispecies," Curr. Topics Microbiol. Immunol. 176:1-20, Abstract Only.

Ide et al. "Peptide-Loaded Dendritic-Cell Vaccination Followed by Treatment Interruption for Chronic HIV-1 Infection: A Phase 1 Trial," Journal of Medical Virology, Jun. 2006, vol. 78, No. 6, pp. 711-718.

Isaguliants, M.G. et al. (Apr. 2004). "Reverse Transcriptase-Based DNA Vaccines Against Drug-Resistant HIV-1 Tested in a Mouse Model," Vaccine 22(13-14):1810-1819.

Johnson, VA et al. (Mar./Apr. 2005). "Update of the Drug Resistance Mutations in HIV-1:2005," International AIDS Society-USA 13(1):51-57.

Kiertscher, S.M. et al. (Feb. 1996). "Human CD14+Leukocytes Acquire the Phenotype and Function of Antigen-Presenting Dendritic Cells when Cultured in GM-CSF and IL-4," J. Leukoc. Biol. 59:208-218.

Kobayashi, S. et al. (Feb. 24, 2005). "EGFR Mutation and Resistance of Non-Small- Cell Lung Cancer to Getitinib," N. Engl. J. Med. 352(8):786-792.

Lalvani, A et al. (Sep. 15, 1997). "Rapid Effector Function in CD8+Memory T Cells," J. Exp. Med. 186(6):859-865.

Lin, C. et al. (Apr. 23, 2004). "In Vitro Resistance Studies of Hepatitis C Virus Serine Protease Inhibitors, VX-950 and BILN 2061," Journal of Biological Chemistry279(17):17508-17514.

Lu, Y. et al. (Aug. 1, 2004). "Mutation-Selective Tumor Remission with Ras-Targeted, Whole Yeast-Based Immunotherapy," Cancer Research, 64:5084-5088.

Mansky, L.M. et al. (Aug. 1995). "Lower In Vivo Mutation Rate of Human Immunodeficiency Virus Type 1 than That Predicted from the Fidelity of Purified Reverse Transcriptase," J. Virol. 69(8):5087-5094.

McKeon, C. et al. (Aug. 20, 1996). "NIDDK Workshop on AAV Vectors: Gene Transfer Into Quiescent Cells," Human Gene Therapy 7:1615-1619.

McMichael, AJ. et al. (May 4, 1998). "A New Look at T Cells," J. Exp. Med. 187(9):1367-1371.

Mittereder, N. et al. (1994). "Evaluation of the Efficacy and Safety of in Vitro Adenovirus-Mediated Transfer of the Human Cystic Fibrosis Transmembrane Conductance ReQulator cDNA," Human Gene Therapy 5:717-729.
Najera, I. et al. (Jan. 1995). "pol Gene Quasispecies of Human Immunodeficiency Virus: Mutations Associated with Drug Resistance in Virus from Patients Undergoing No Drug Therapy," J. Virol. 69(1):23-31.
Nakai, H. et al. (Aug. 2001). "Extrachromosomal Recombinant Adeno-Associated Virus Vector Genomes Are Primarily Responsible for Stable Liver Transduction in Vivo," J. Virol. 75(15):6969-6976.
Okazaki, T. et al. (Nov. 2006). "Possible Therapeutic Vaccine Strategy Against Human Immunodeficiency Virus Escape From Reverse Transcriptase Inhibitors Studied in HLA-A2 Transgenic Mice," Journal of Virology 80(21):10645-10651.
Rich, D.P. et al. (1993). "Development and Analysis of Recombinant Adenoviruses for Gene Therapy of Cystic Fibrosis," Human Gene Therapy 4:461-476.
Richman, D.D. et al. (1990). "Effect of Stage of Disease and Drug Dose on Zidovudine Susceptibilities of Isolates of Human Immunodeficiency virus," J. AIDS 3(8):743-746, Abstract Only.
Romani, N. et al. (Jul. 1, 1994). "Proliferating Dendritic Cell Progenitors in Human Blood," J. Exp. Med. 180:83-93.
Schmitt, M. et al. (2000). "Specific Recognition of Lamivudine-Resistant HIV-1 by Cytotoxic T Lymphocytes," AIDS 14(6):653-658.
Schnepp, B.C. et al. (Mar. 2003). "Genetic Fate of Recombinant Adeno-Associated Virus Vector Genomes in Muscle," J. Virol. 77(6):3495-3504.
Segota, E. et al. (Jul. 2004). "The Promise of Targeted Therapy: Cancer Drugs Become More Specific," Cleveland Clinic J. Med. 71 (7):551-560.
Seth, P. et al. (Feb. 1994). "Mechanism of Enhancement of DNA Expression Consequent to Cointernalization of a Replication-Deficient Adenovirus and Unmodified Plasmid DNA," J. Virol. 68(2):933-940.
Shah, N.P. et al. (Aug. 2002). "Multiple BCR-ABL Kinase Domain Mutations Confer Polyclonal Resistance to the Tyrosine Kinase Inhibitor Imatinib (STI671) in Chronic Phase and Blast Crisis Chronic Myeloid Leukemia," Cancer Cell 2:117-125.
Snyder, R. et al. (Nov. 1, 1997). "Efficient and Stable Adeno-Associated Virus- Mediated Transduction in the Skeletal Muscle of Adult Immunocompetent Mice," Human Gene Therapy 8:1891-1900.
Stribling, R. et al. (Dec. 1992). "Aerosol Gene Delivery in Vivo," Proc. Natl. Acad. Sci.USA 89:11277-11281.
Stubbs, A.C. et al. (May 2001). "Whole Recombinant Yeast Vaccine Activates Dendricitc Cells and Elicits Protective Cell Mediated Immunity," Nature Med. 5(7):1-5.
Tachedjian, G. et al. (Jun. 19, 2001). "Nonnucleoside Reverse Transcriptase Inhibitors are Chemical Enhancers of Dimerization of the HIV Type 1 Reverse Transcriptase," PNAS USA 98(13):7188-7193.
Takeda, K. et al. (2005). "Toll-Like Receptors in Innate Immunity," International Immunology 17(1):1-14.
Tamborini, E. et al. (2004). "A New Mutation in the KIT ATP Pocket Causes Acquired Resistance to Imatinib in a Gastrointestinal Stromal Tumor Patient," Gastroenterology 127:294299.
Thyphronitis, G. et al. (Jul.-Aug. 2004). "Boosting the Immune Response: An alternative Combination Therapy for Cancer Patients," Anticancer Research 24(4):2443-2453, Abstract Only.
Trono, D. (Jul. 28, 1995). "HIV Accessory Proteins: Leading Roles for the Supporting Cast," Cell, 82:189-192.
Vincent-Lacaze, N. et al. (Mar. 1999). "Structure of Adeno-Associated Virus Vector DNA Following Transduction of the Skeletal Muscle," J. Viral. 73(3):1949-1955.
Walz, C. et al. (2006). "Novel Targeted Therapies to Overcome Imatinib Mesylate Resistance in Chronic Myeloid Leukemia (CML)," Critical Reviews in Oncology/Hematology 57:145-164.
Wilson, C.C. et al. (1999). "HIV-1-Specific CTL Responses Primed In Vitro by Blood-Derived Dendricitc Cells and Th1-Biasing Cytokines," Immunol. 162:3070-3078.
International Search Report mailed on Jan. 26, 2007, for PCT Application No. PCT/US2006/026710, filed on Jul. 10, 2006, 3 pages.
Written Opinion of the International Searching Authority mailed on Jan. 26, 2007, for PCT Application No. PCT/US2006/026710, filed on Jul. 10, 2006, 9 pages.
International Search Report mailed on Aug. 20, 2008, for PCT Application No. PCT/US2008/051348, filed on Jan. 17, 2008, 4 pages.
Written Opinion of the International Searching Authority mailed on Aug. 20, 2008, for PCT Application No. PCT/US2008/051348, filed on Jan. 17, 2008, 6 pages.
Official Action for European Patent Application No. 06786760.6, dated Apr. 9, 2009 2 pages.
International Preliminary Report on Patentability mailed on Oct. 1, 2009, for PCT Application No. PCT/US2008/051348, filed on Jan. 17, 2008, 7 pages.
English translation of Official Action for Israel Patent Application No. 188717, dated Apr. 14, 2010 1 page.
Official Action with English translation of China Patent Application No. 2006800331652, dated May 27, 2010 4 pages.
Official Action for European Patent Application No. 08713806.1, dated Aug. 10, 2010 4 pages.
Official Action for Australia Patent Application No. 2006268333, dated May 10, 2011 2 pages.
English translation of Official Action for Israel Patent Application No. 188717, dated Nov. 18, 2010 3 pages.
Bizzini et al. "Use of live *Saccharomyces cerebisiae* cells as a biological response modifier in experimental infections," FEMS Microbiology Immunology, Oct. 1990, vol. 64, No. 3, pp. 155-168.
Brake et al. "a-Factor-directed synthesis and secretion of mature foreign proteins in *Saccharomyces cerevisiae*." PNAS, Aug. 1984, vol. 81, pp. 4642-4646.
Caspar et al. "Idiotype Vaccines for Non-Hodgkin's Lymphoma Induce Polyclonal Immune Responses That Cover Mutated Tumor Idiotypes: Comparison of Different Vaccine Formulations," Blood, Nov. 1, 1997, vol. 90, No. 9, pp. 3699-3706.
ETO et al. Immunization with Recombinant *Escherichia coli* Expressing Retinal S-Antigen-Induced Experimental Autoimmune Uveitis (EAU) in Lewis Rats, Cellular Immunology, Mar. 1993, vol. 147, No. 1, pp. 203-214.
Franzusoff et al. "Biochemical and Genetic Definition of the Cellular Protease Required for HIV-1 gp160 Processing," The Journal of Biological Chemistry, Feb. 17, 1995, vol. 270, No. 7, pp. 3154-3159.
Fujita et al. "Studies in the development of Japanese encephalitis vaccine: expression of virus envelope glycoprotein V3 (E) gene in yeast." Bulletin of the World Health Organization, Feb. 1987, vol. 65, No. 3, pp. 303-308.
Klepfer et al. "Characterization of rabies glycoprotein expressed in yeast." Archives of Virology, 1993, vol. 128, No. 3-4, pp. 269-286.
Moore et al. "Novel yeast-based vaccine against HIV-SF2 gp160 promotes a cytotoxic 43-62 cell response." FASEB Journal 1996, vol. 10, No. 6, p. A1473 ZP002186594.
Schreuder et al. "Yeast expressing hepatitis B virus surface antigen determinants on its surface: implications for a possible oral vaccine." Vaccine, Apr. 1996, vol. 14, No. 5, pp. 383-388.
Sheu et al. "Tumor Immunology-When a Cancer Cell Meets the Immune Cells," Journal of the Formosan Medical Association, Nov. 1999, vol. 98, No. 11, pp. 730-735.
Sinai et al. "Enhancement of Resistance to Infectious Diseases by Oral Administration of Brewer's Yeast," Infection and Immunity, May 1974, vol. 9, No. 5, pp. 781-787.
Thyphronitis et al. "Boosting the Immune Response: An Alternative Combination Therapy for Cancer Patients," Anticancer Research, Jul.-Aug. 2004, vol. 24, pp. 2443-2454.
Valenzuela et al. "Antigen engineering in yeast: Synthesis and assembly of hybrid hepatitis B surface antigen-Herpes simplex 1 gD particles," Bio/Technology, Apr. 1985, vol. 3, pp. 323-326.
Official Action for New Zealand Patent Application No. 580444, dated Oct. 3, 2011 2 pages.
Notice of Allowance for New Zealand Patent Application No. 580444, dated Jan. 25, 2012 1 page.
English translation of Official Action for China Patent Application No. 200680033165.2, dated Feb. 17, 2012 5 pages.
Official Action for U.S. Appl. No. 12/067,802, mailed Feb. 6, 2012 10 pages.

* cited by examiner

SEQUENCE LISTING

```
<160> NUMBER OF SEQ ID NOS: 6

<210> SEQ ID NO 1
<211> LENGTH: 340
<212> TYPE: PRT
<213> ORGANISM: Artificial Sequence
<220> FEATURE:
<223> OTHER INFORMATION: Synthetic Construct

<400> SEQUENCE: 1

Met Ala Asp Glu Ala Pro Asn Leu Phe Val Ala Leu Tyr Asp Phe Val
 1               5                  10                  15

Ala Ser Gly Asp Asn Thr Leu Ser Ile Thr Lys Gly Glu Lys Leu Arg
            20                  25                  30

Val Leu Gly Tyr Asn His Asn Gly Glu Trp Cys Glu Ala Gln Thr Lys
        35                  40                  45

Asn Gly Gln Gly Trp Val Pro Ser Asn Tyr Ile Thr Pro Val Asn Ser
    50                  55                  60

Leu Glu Lys His Ser Trp Tyr His Gly Pro Val Ser Arg Asn Ala Ala
65                  70                  75                  80

Glu Tyr Leu Leu Ser Ser Gly Ile Asn Gly Ser Phe Leu Val Arg Glu
                85                  90                  95

Ser Glu Ser Ser Pro Gly Gln Arg Ser Ile Ser Leu Arg Tyr Glu Gly
            100                 105                 110

Arg Val Tyr His Tyr Arg Ile Asn Thr Ala Ser Asp Gly Lys Leu Tyr
        115                 120                 125

Val Ser Ser Glu Ser Arg Phe Asn Thr Leu Ala Glu Leu Val His His
    130                 135                 140

His Ser Thr Val Ala Asp Gly Leu Ile Thr Thr Leu His Tyr Pro Ala
145                 150                 155                 160

Pro Lys Arg Asn Lys Pro Thr Ile Tyr Gly Val Ser Pro Asn Tyr Asp
                165                 170                 175

Lys Trp Glu Met Glu Arg Thr Asp Ile Thr Met Lys His Lys Leu Gly
            180                 185                 190

Gly Gly Gln Tyr Gly Lys Val Tyr Glu Gly Val Trp Lys Lys Tyr Ser
        195                 200                 205

Leu Thr Val Ala Val Lys Thr Leu Lys Glu Asp Thr Met Glu Val Glu
```

```
                 210                 215                 220
Glu Phe Leu Lys Glu Ala Ala Val Met Lys Glu Ile Lys His Pro Asn
225                 230                 235                 240

Leu Val Gln Leu Leu Gly Val Cys Thr Arg Glu Pro Pro Phe Tyr Ile
                245                 250                 255

Ile Ile Glu Phe Met Thr Tyr Gly Asn Leu Leu Asp Tyr Leu Arg Glu
                260                 265                 270

Cys Asn Arg Gln Glu Val Ser Ala Val Leu Leu Tyr Met Ala Thr
            275                 280                 285

Gln Ile Ser Ser Ala Thr Glu Tyr Leu Glu Lys Lys Asn Phe Ile His
            290                 295                 300

Arg Asp Leu Ala Ala Arg Asn Cys Leu Val Gly Glu Asn His Leu Val
305                 310                 315                 320

Lys Val Ala Asp Phe Gly Leu Ser Arg Leu Met Thr Gly Asp His His
                325                 330                 335

His His His His
        340

<210> SEQ ID NO 2
<211> LENGTH: 340
<212> TYPE: PRT
<213> ORGANISM: Artificial Sequence
<220> FEATURE:
<223> OTHER INFORMATION: Synthetic Construct

<400> SEQUENCE: 2

Met Ala Asp Glu Ala Pro Asn Leu Phe Val Ala Leu Tyr Asp Phe Val
1               5                   10                  15

Ala Ser Gly Asp Asn Thr Leu Ser Ile Thr Lys Gly Glu Lys Leu Arg
            20                  25                  30

Val Leu Gly Tyr Asn His Asn Gly Glu Trp Cys Glu Ala Gln Thr Lys
        35                  40                  45

Asn Gly Gln Gly Trp Val Pro Ser Asn Tyr Ile Thr Pro Val Asn Ser
50                  55                  60

Leu Glu Lys His Ser Trp Tyr His Gly Pro Val Ser Arg Asn Ala Ala
65                  70                  75                  80

Glu Tyr Leu Leu Ser Ser Gly Ile Asn Gly Ser Phe Leu Val Arg Glu
                85                  90                  95

Ser Glu Ser Ser Pro Gly Gln Arg Ser Ile Ser Leu Arg Tyr Glu Gly
            100                 105                 110

Arg Val Tyr His Tyr Arg Ile Asn Thr Ala Ser Asp Gly Lys Leu Tyr
        115                 120                 125

Val Ser Ser Glu Ser Arg Phe Asn Thr Leu Ala Glu Leu Val His His
130                 135                 140

His Ser Thr Val Ala Asp Gly Leu Ile Thr Thr Leu His Tyr Pro Ala
145                 150                 155                 160

Pro Lys Arg Asn Lys Pro Thr Ile Tyr Gly Val Ser Pro Asn Tyr Asp
                165                 170                 175

Lys Trp Glu Met Glu Arg Thr Asp Ile Thr Met Lys His Lys Leu Gly
            180                 185                 190

Gly Gly Gln Tyr Gly Glu Val Tyr Glu Gly Val Trp Lys Lys Tyr Ser
        195                 200                 205

Leu Thr Val Ala Val Lys Thr Leu Lys Glu Asp Thr Met Glu Val Glu
210                 215                 220

Glu Phe Leu Lys Glu Ala Ala Val Met Lys Glu Ile Lys His Pro Asn
225                 230                 235                 240
```

```
Leu Val Gln Leu Leu Gly Val Cys Thr Arg Glu Pro Pro Phe Tyr Ile
                245                 250                 255

Ile Ile Glu Phe Met Thr Tyr Gly Asn Leu Leu Asp Tyr Leu Arg Glu
            260                 265                 270

Cys Asn Arg Gln Glu Val Ser Ala Val Val Leu Leu Tyr Met Ala Thr
            275                 280                 285

Gln Ile Ser Ser Ala Met Glu Tyr Leu Glu Lys Lys Asn Phe Ile His
        290                 295                 300

Arg Asp Leu Ala Ala Arg Asn Cys Leu Val Gly Glu Asn His Leu Val
305                 310                 315                 320

Lys Val Ala Asp Phe Gly Leu Ser Arg Leu Met Thr Gly Asp His His
                325                 330                 335

His His His His
        340

<210> SEQ ID NO 3
<211> LENGTH: 437
<212> TYPE: PRT
<213> ORGANISM: Artificial Sequence
<220> FEATURE:
<223> OTHER INFORMATION: Synthetic Construct

<400> SEQUENCE: 3

Met Ala Asp Glu Ala Pro Cys Phe Arg Ser Phe Ser Leu Thr Ser Val
 1               5                  10                  15

Glu Gln Gln Met Leu Thr Asn Ser Cys Val Lys Leu Gln Thr Val His
             20                  25                  30

His Ile Pro Leu Thr Ile Asn Lys Glu Asp Asp Glu Ser Pro Gly Leu
         35                  40                  45

Tyr Gly Phe Leu His Val Ile Val His Ser Ala Thr Gly Phe Lys Gln
     50                  55                  60

Ser Ser Lys Ala Leu Gln Arg Pro Val Ala Ser Asp Phe Glu Pro Gln
65                  70                  75                  80

Gly Leu Ser Glu Ala Ala Arg Trp Asn Ser Lys Glu Asn Leu Leu Ala
                 85                  90                  95

Gly Pro Ser Glu Asn Asp Pro Asn Leu Phe Val Ala Leu Tyr Asp Phe
            100                 105                 110

Val Ala Ser Gly Asp Asn Thr Leu Ser Ile Thr Lys Gly Glu Lys Leu
        115                 120                 125

Arg Val Leu Gly Tyr Asn His Asn Gly Glu Trp Cys Glu Ala Gln Thr
130                 135                 140

Lys Asn Gly Gln Gly Trp Val Pro Ser Asn Tyr Ile Thr Pro Val Asn
145                 150                 155                 160

Ser Leu Glu Lys His Ser Trp Tyr His Gly Pro Val Ser Arg Asn Ala
                165                 170                 175

Ala Glu Tyr Leu Leu Ser Ser Gly Ile Asn Gly Ser Phe Leu Val Arg
            180                 185                 190

Glu Ser Glu Ser Ser Pro Gly Gln Arg Ser Ile Ser Leu Arg Tyr Glu
        195                 200                 205

Gly Arg Val Tyr His Tyr Arg Ile Asn Thr Ala Ser Asp Gly Lys Leu
    210                 215                 220

Tyr Val Ser Ser Glu Ser Arg Phe Asn Thr Leu Ala Glu Leu Val His
225                 230                 235                 240

His His Ser Thr Val Ala Asp Gly Leu Ile Thr Thr Leu His Tyr Pro
                245                 250                 255
```

```
Ala Pro Lys Arg Asn Lys Pro Thr Ile Tyr Gly Val Ser Pro Asn Tyr
            260                 265                 270

Asp Lys Trp Glu Met Glu Arg Thr Asp Ile Thr Met Lys His Lys Leu
        275                 280                 285

Gly Gly Gly Gln Tyr Gly Glu Val Tyr Glu Gly Val Trp Lys Lys Tyr
        290                 295                 300

Ser Leu Thr Val Ala Val Lys Thr Leu Lys Glu Asp Thr Met Glu Val
305                 310                 315                 320

Glu Glu Phe Leu Lys Glu Ala Ala Val Met Lys Glu Ile Lys His Pro
                325                 330                 335

Asn Leu Val Gln Leu Leu Gly Val Cys Thr Arg Glu Pro Pro Phe Tyr
                340                 345                 350

Ile Ile Thr Glu Phe Met Thr Tyr Gly Asn Leu Leu Asp Tyr Leu Arg
                355                 360                 365

Glu Cys Asn Arg Gln Glu Val Ser Ala Val Val Leu Leu Tyr Met Ala
            370                 375                 380

Thr Gln Ile Ser Ser Ala Met Glu Tyr Leu Glu Lys Lys Asn Phe Ile
385                 390                 395                 400

His Arg Asp Leu Ala Ala Arg Asn Cys Leu Val Gly Glu Asn His Leu
                405                 410                 415

Val Lys Val Ala Asp Phe Gly Leu Ser Arg Leu Met Thr Gly Asp His
                420                 425                 430

His His His His His
            435

<210> SEQ ID NO 4
<211> LENGTH: 340
<212> TYPE: PRT
<213> ORGANISM: Artificial Sequence
<220> FEATURE:
<223> OTHER INFORMATION: Synthetic Construct

<400> SEQUENCE: 4

Met Ala Asp Glu Ala Pro Asn Leu Phe Val Ala Leu Tyr Asp Phe Val
1               5                   10                  15

Ala Ser Gly Asp Asn Thr Leu Ser Ile Thr Lys Gly Glu Lys Leu Arg
                20                  25                  30

Val Leu Gly Tyr Asn His Asn Gly Glu Trp Cys Glu Ala Gln Thr Lys
            35                  40                  45

Asn Gly Gln Gly Trp Val Pro Ser Asn Tyr Ile Thr Pro Val Asn Ser
        50                  55                  60

Leu Glu Lys His Ser Trp Tyr His Gly Pro Val Ser Arg Asn Ala Ala
65                  70                  75                  80

Glu Tyr Leu Leu Ser Ser Gly Ile Asn Gly Ser Phe Leu Val Arg Glu
                85                  90                  95

Ser Glu Ser Ser Pro Gly Gln Arg Ser Ile Ser Leu Arg Tyr Glu Gly
                100                 105                 110

Arg Val Tyr His Tyr Arg Ile Asn Thr Ala Ser Asp Gly Lys Leu Tyr
            115                 120                 125

Val Ser Ser Glu Ser Arg Phe Asn Thr Leu Ala Glu Leu Val His His
130                 135                 140

His Ser Thr Val Ala Asp Gly Leu Val Thr Thr Leu His Tyr Pro Ala
145                 150                 155                 160

Pro Lys Arg Asn Lys Pro Thr Ile Tyr Gly Val Ser Pro Asn Tyr Asp
                165                 170                 175

Lys Trp Glu Met Glu Arg Thr Asp Ile Thr Met Lys His Lys Leu Gly
```

```
                180                 185                 190
Gly Gly Gln Tyr Gly Glu Val Tyr Glu Gly Val Trp Lys Lys Tyr Ser
            195                 200                 205

Leu Thr Val Ala Val Lys Thr Leu Lys Glu Asp Thr Met Glu Val Glu
        210                 215                 220

Glu Phe Leu Lys Glu Ala Ala Val Met Lys Glu Ile Lys His Pro Asn
225                 230                 235                 240

Leu Val Gln Leu Leu Gly Val Cys Thr Arg Glu Pro Pro Phe Tyr Ile
                245                 250                 255

Ile Ile Glu Phe Met Thr Tyr Gly Asn Leu Leu Asp Tyr Leu Arg Glu
            260                 265                 270

Cys Asn Arg Gln Glu Val Asn Ala Val Val Leu Leu Tyr Met Ala Thr
        275                 280                 285

Gln Ile Ser Ser Ala Met Glu Tyr Leu Glu Lys Lys Asn Phe Ile His
        290                 295                 300

Arg Asp Leu Ala Ala Arg Asn Cys Leu Val Gly Glu Asn His Leu Val
305                 310                 315                 320

Lys Val Ala Asp Phe Gly Leu Ser Arg Leu Met Thr Gly Asp His His
                325                 330                 335

His His His His
        340

<210> SEQ ID NO 5
<211> LENGTH: 437
<212> TYPE: PRT
<213> ORGANISM: Artificial Sequence
<220> FEATURE:
<223> OTHER INFORMATION: Synthetic Construct

<400> SEQUENCE: 5

Met Ala Asp Glu Ala Pro Cys Phe Arg Ser Phe Ser Leu Thr Ser Val
1               5                   10                  15

Glu Leu Gln Met Leu Thr Asn Ser Cys Val Lys Leu Gln Thr Val His
                20                  25                  30

Ser Ile Pro Leu Thr Ile Asn Lys Glu Asp Asp Glu Ser Pro Gly Leu
            35                  40                  45

Tyr Gly Phe Leu His Val Ile Val His Ser Ala Thr Gly Phe Lys Gln
        50                  55                  60

Ser Ser Lys Ala Leu Gln Arg Pro Val Ala Ser Asp Phe Glu Pro Gln
65                  70                  75                  80

Gly Leu Ser Glu Ala Ala Arg Trp Asn Ser Lys Glu Asn Leu Leu Ala
                85                  90                  95

Gly Pro Ser Glu Asn Asp Pro Asn Leu Phe Val Ala Leu Tyr Asp Phe
            100                 105                 110

Val Ala Ser Gly Asp Asn Thr Leu Ser Ile Thr Lys Gly Glu Lys Leu
        115                 120                 125

Arg Val Leu Gly Tyr Asn His Asn Gly Glu Trp Cys Glu Ala Gln Thr
    130                 135                 140

Lys Asn Gly Gln Gly Trp Val Pro Ser Asn Tyr Ile Thr Pro Val Asn
145                 150                 155                 160

Ser Leu Glu Lys His Ser Trp Tyr His Gly Pro Val Ser Arg Asn Ala
                165                 170                 175

Ala Glu Tyr Leu Leu Ser Ser Gly Ile Asn Gly Ser Phe Leu Val Arg
            180                 185                 190

Glu Ser Glu Ser Ser Pro Gly Gln Arg Ser Ile Ser Leu Arg Tyr Glu
        195                 200                 205
```

-continued

```
Gly Arg Val Tyr His Tyr Arg Ile Asn Thr Ala Ser Asp Gly Lys Leu
        210                 215                 220

Tyr Val Ser Ser Glu Ser Arg Phe Asn Thr Leu Ala Glu Leu Val His
225                 230                 235                 240

His His Ser Thr Val Ala Asp Gly Leu Ile Thr Thr Leu His Tyr Pro
                245                 250                 255

Ala Pro Lys Arg Asn Lys Pro Thr Val Tyr Gly Val Ser Pro Asn Tyr
            260                 265                 270

Asp Lys Trp Glu Met Glu Arg Thr Asp Ile Thr Met Lys His Lys Leu
        275                 280                 285

Gly Gly Gly Gln Tyr Gly Glu Val Tyr Glu Gly Val Trp Lys Lys Tyr
        290                 295                 300

Ser Leu Thr Val Ala Val Lys Thr Leu Lys Glu Asp Thr Met Glu Val
305                 310                 315                 320

Glu Glu Phe Leu Lys Glu Ala Ala Val Met Lys Glu Ile Lys His Pro
                325                 330                 335

Asn Leu Val Gln Leu Leu Gly Val Cys Thr Arg Glu Pro Pro Phe Tyr
            340                 345                 350

Ile Ile Thr Glu Phe Met Thr Tyr Gly Asn Leu Leu Asp Tyr Leu Arg
        355                 360                 365

Glu Cys Asn Arg Gln Glu Val Asn Ala Val Val Leu Leu Tyr Met Ala
        370                 375                 380

Thr Gln Ile Ser Ser Ala Met Glu Tyr Leu Glu Lys Lys Asn Phe Ile
385                 390                 395                 400

His Arg Asp Leu Ala Ala Arg Asn Cys Leu Val Gly Glu Asn His Leu
                405                 410                 415

Val Lys Val Ala Asp Phe Gly Leu Ser Arg Leu Met Thr Gly Asp His
            420                 425                 430

His His His His His
        435

<210> SEQ ID NO 6
<211> LENGTH: 340
<212> TYPE: PRT
<213> ORGANISM: Artificial Sequence
<220> FEATURE:
<223> OTHER INFORMATION: Synthetic Construct

<400> SEQUENCE: 6

Met Ala Asp Glu Ala Pro Asn Leu Phe Val Ala Leu Tyr Asp Phe Val
1               5                   10                  15

Ala Ser Gly Asp Asn Thr Leu Ser Ile Thr Lys Gly Glu Lys Leu Arg
            20                  25                  30

Val Leu Gly Tyr Asn His Asn Gly Glu Trp Cys Glu Ala Gln Thr Lys
        35                  40                  45

Asn Gly Gln Gly Trp Val Pro Ser Asn Tyr Ile Thr Pro Val Asn Ser
    50                  55                  60

Leu Glu Lys His Ser Trp Tyr His Gly Pro Val Ser Arg Asn Ala Ala
65                  70                  75                  80

Glu Tyr Leu Leu Ser Ser Gly Ile Asn Gly Ser Phe Leu Val Arg Glu
                85                  90                  95

Ser Glu Ser Ser Pro Gly Gln Arg Ser Ile Ser Leu Arg Tyr Glu Gly
            100                 105                 110

Arg Val Tyr His Tyr Arg Ile Asn Thr Ala Ser Asp Gly Lys Leu Tyr
        115                 120                 125
```

-continued

```
Val Ser Ser Glu Ser Arg Phe Asn Thr Leu Ala Glu Leu Val His His
    130                 135             140
His Ser Thr Val Ala Asp Gly Leu Ile Thr Thr Leu His Tyr Pro Ala
145             150                 155                 160
Pro Lys Arg Asn Lys Pro Thr Val Tyr Gly Val Ser Pro Asn Tyr Asp
                165                 170             175
Lys Trp Glu Met Glu Arg Thr Asp Ile Thr Met Lys His Lys Leu Gly
            180                 185             190
Gly Gly Gln Tyr Gly Lys Val Tyr Glu Gly Val Trp Lys Lys Tyr Ser
        195                 200             205
Leu Thr Val Ala Val Lys Thr Leu Lys Glu Asp Thr Met Glu Val Glu
    210                 215             220
Glu Phe Leu Lys Glu Ala Ala Val Met Lys Glu Ile Lys His Pro Asn
225             230                 235                 240
Leu Val Gln Leu Leu Gly Val Cys Thr Arg Glu Pro Pro Phe Tyr Ile
                245                 250             255
Ile Ile Glu Phe Met Thr Tyr Gly Asn Leu Leu Asp Tyr Leu Arg Glu
            260                 265             270
Cys Asn Arg Gln Glu Val Asn Ala Val Val Leu Leu Tyr Met Ala Thr
        275                 280             285
Gln Ile Ser Ser Ala Thr Glu Tyr Leu Glu Lys Lys Asn Phe Ile His
    290                 295             300
Arg Asp Leu Ala Ala Arg Asn Cys Leu Val Gly Glu Asn His Leu Val
305             310                 315                 320
Lys Val Ala Asp Phe Gly Leu Ser Arg Leu Met Thr Gly Asp His His
                325                 330             335
His His His His
        340
```

COMPOSITIONS AND METHODS FOR TARGETED ABLATION OF MUTATIONAL ESCAPE OF TARGETED THERAPIES FOR CANCER

CROSS-REFERENCE TO RELATED APPLICATIONS

This application is a national stage application under 35 U.S.C. §371 of PCT Application No. PCT/US2008/051348, having an international filing date of Jan. 17, 2008, which designated the United States, and which PCT application claims the benefit of priority under 35 U.S.C. §119(e) from each of U.S. Provisional Application No. 60/895,689, filed Mar. 19, 2007 and U.S. Provisional Application No. 60/910,796, filed Apr. 9, 2007.

TECHNICAL FIELD

The present invention generally relates to compositions and methods for their use in combination with cancer therapeutic agents to achieve targeted ablation of mutational escape.

BACKGROUND OF THE INVENTION

Novel discoveries in cancer biology have provided the opportunity to design target-specific anti-cancer agents and fostered advancements in drug development. These discoveries make it possible to design molecules with high selectivity against specific targets in cancer cells. Segota & Bukowski, *Cleveland Clinic J. Med.*, 71(7):551-560 (2004). For example, the success of the Bcr-Abl tyrosine kinase inhibitor imatinib (Gleevec) in the treatment of chronic myeloid leukemia (CML) has inspired great expectation for this targeted approach. Capdeville et al., *Nature Reviews*, 1:493-502 (2002). Targeted cancer therapy brings with it a critical problem: targets develop escape mutations ultimately leading to drug resistance. For example, it has been reported that mutations have been found to arise in patients that were initially responsive to treatment with Gleevec and who as a result of these mutations are refractory to further treatment with Gleevec. Gone et al., *Science*, 293:876-880 (2001); Shah et al., *Cancer Cell*, 2:117-125 (2002); Branford et al., *Blood*, 99(9):3742-3745 (2002); Deininger et al., *Blood*, 105(7):2640-263 (2005); Walz et al., *Critical Reviews in Oncology/Hematology* 57:145-164 (2006); and Burgess et al., *The Scientific World JOURNAL*, 6:918-930 (2006). Similarly, mutations in epidermal growth factor receptor (EGFR) have been found in non-small cell lung cancer (NSCLC) patients that were reported to make them resistant to the action of therapeutic agents such as gefitinib (Iressa) or erlotinib (Tarceva) that specifically target EGFR. Kobayashi et al., *N. Engl. J. Med.*, 352(8):786-792 (2005). Therefore, the effectiveness of these cancer drugs is significantly limited by the occurrence of escape mutations.

As such, it would be desirable to at least minimize the occurrence of mutants that emerge with the administration of therapeutic and/or prophylactic agents.

Methods for eliciting an immune response are disclosed in for example, Thyphronitis et al., *Anticancer Research*, Vol. 24:2443-2454 (2004) and Plate et al., *Journal of Cell Biology*, Vol. 94:1069 (2005). Yeast systems are disclosed in for example, U.S. Pat. No. 5,830,463, Stubbs et al., *Nature Med.* 5:625-629 (2001); Lu et al., *Cancer Research* 64:5084-5088 (2004); and Franzusoff, et al., *Expert Opin. Bio. Ther.* Vol. 5:565-575 (2005).

All references cited herein, including patents, patent applications and publications, are hereby incorporated by reference in their entirety.

BRIEF SUMMARY OF THE INVENTION

Provided herein are compositions and methods for targeted ablation of a mutational escape associated with cancer. In one aspect, the invention provides methods for targeting the ablation of a mutational escape in an individual in need thereof by administering to the individual an effective amount of a targeted therapeutic agent wherein the therapeutic agent is selected from the group consisting of a tyrosine kinase inhibitor, a Src kinase inhibitor, an agent that affects Bcr-Abl stability, and an agent that acts in a signaling pathway that is downstream of Bcr-Abl and a composition comprising one or more of the following: i) a yeast vehicle comprising nucleic acid which encodes at least one mutant polypeptide associated with cancer, a fragment thereof that comprises a mutation, or a mimetope; ii) a yeast vehicle comprising at least one mutant polypeptide associated with cancer, a fragment thereof that comprises a mutation, or a mimetope; iii) a yeast vehicle in association with at least one mutant polypeptide associated with cancer, a fragment thereof that comprises a mutation, or a mimetope; iv) a yeast vehicle comprising nucleic acid which encodes at least one mutant polypeptide associated with cancer, a fragment thereof that comprises a mutation, or a mimetope loaded intracellularly into a dendritic cell; or v) a yeast vehicle and at least one mutant polypeptide associated with cancer, a fragment thereof that comprises a mutation, or a mimetope loaded intracellularly into a dendritic cell, wherein the mutant polypeptide is known to emerge or has emerged with at least one specific mutation in response to administration of a targeted therapeutic and/or prophylactic agent for cancer. In some aspects, the targeted therapeutic agent is a tyrosine kinase inhibitor. In one aspect, the tyrosine kinase inhibitor is imatinib. In other aspects, the tyrosine kinase inhibitor is selected from the group consisting of imatinib, nilotinib, PD1866326, PD180970, AP23464, BMS-354825, ON012380, VX-680, and BIRB-796.

In another aspect, the targeted therapeutic agent is a Src kinase inhibitor. In some examples, the Src kinase inhibitor is selected from the group consisting of PD166326, PD180970, AP23464, BMS-354825, AZM475271, PP1, PP2, AP-23236, CGP76030, and PD173955. In another aspect, the targeted therapeutic agent is PKC412 or SU11248. In other aspects, the targeted therapeutic agent affects Bcr-Abl stability. In some examples, the agent targets heat shock proteins or other chaperone proteins that associate with Bcr-Abl. In other examples, the agent is Geldanamycin/17-AAG or NVP-LAQ824.

In another aspect, the targeted therapeutic agent acts in a signaling pathway that is downstream of Bcr-Abl. In some examples, the agent is selected from the group consisting of SCH66336, BAY-439006, CI-1040, LY294002, wortmannin, OSU-03012, CCI-779, R115777, BMS-214662, U0126, PD184352, rapamycin, RAD001, CCI-779, and AP23573.

The invention also provides for kits for targeted ablation of mutational escape associated with cancer in an individual wherein the mutant escape is known to emerge or has emerged with at least one specific mutation in response to administration of a targeted therapeutic and/or prophylactic agent and wherein the kit comprises a composition of any one of the therapeutic agents above.

The invention also provides for kits for targeted ablation of mutational escape associated with cancer in an individual wherein the mutant escape is known to emerge or has emerged with at least one specific mutation in response to administration of a targeted therapeutic and/or prophylactic agent and wherein the kit comprises a yeast vehicle and at least one mutant polypeptide, fragments thereof that comprises a mutation, or mimetopes. In one aspect, the kit further comprises a targeted therapeutic and/or prophylactic agent. In another aspect, the kit further comprises instructional material for the use of the kit.

DETAILED DESCRIPTION OF THE INVENTION

Figure 1:
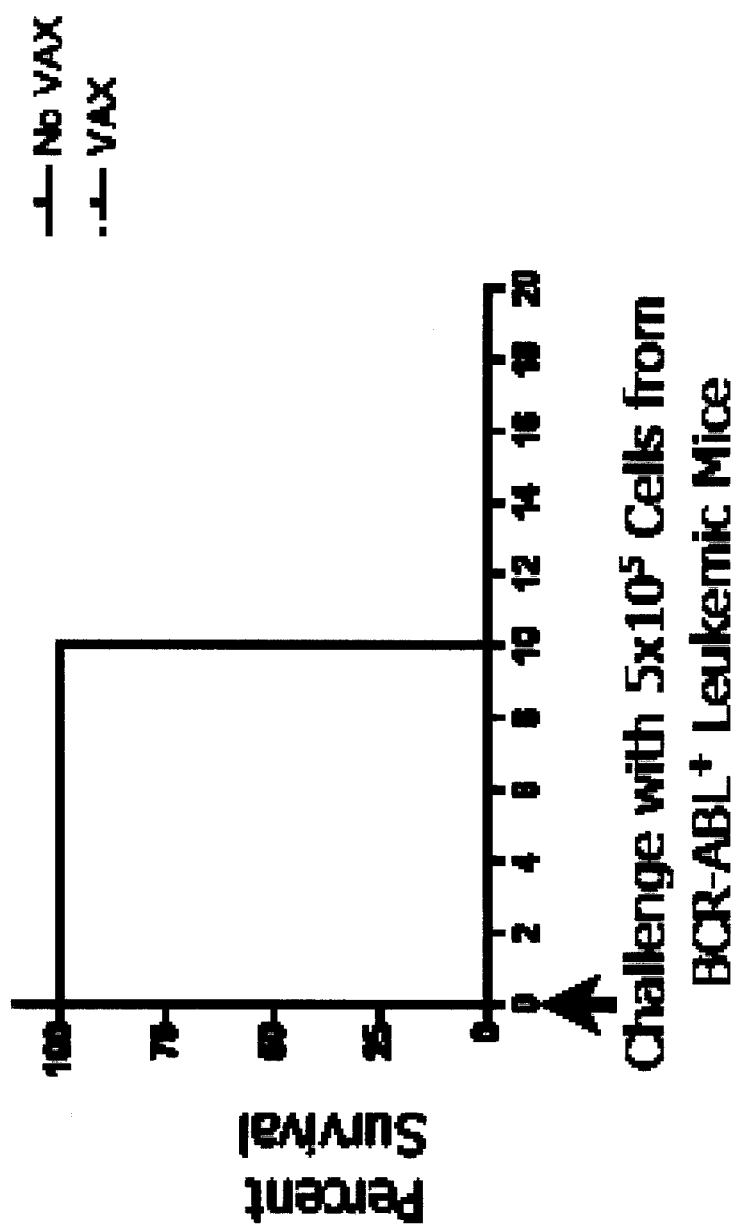
FIG. 1 depicts a survival curve against wild type BCR-ABL leukemia for control vs. vaccinated mice.

There is a need for prophylactic and therapeutic drug agents that specifically target pathways that are unique to tumor cells, but there is a shortcoming in that the tumor cells undergo mutation(s) that allow them to escape the drug agent(s) and/or become resistant. Provided herein are compositions and methods for targeted ablation of mutational escape associated with the prophylactic or therapeutic agents (also referred to herein as a mutant polypeptide). These compositions and methods can be use for eliciting an immune response to a mutant polypeptide that is known to emerge or that has emerged in response to a targeted drug agent, or to a cell that expresses the mutant polypeptide. In some examples, the immune response is a cellular immune response, in some examples the immune response is a humoral response, and in other example the immune response is both cellular and humoral. In some examples, the cellular immune response is intended to eliminate the cell, such as for example, a cancer cell or a cell that supports tumor progression that has escaped control and comprises mutations in the polypeptide targeted by the drug agent, but cell elimination is not required. In some examples, the cellular and/or humoral immune response will block cell proliferation or replication.

Accordingly, provided herein are methods for eliciting an immune response to a mutant polypeptide, or a cell that comprises nucleic acid encoding a mutant polypeptide and/or expresses a mutant polypeptide, that is known to emerge or has emerged with a specific mutation in response to administration of a therapeutic and/or prophylactic agent(s). In some examples, the immune response is a cellular immune response. In some examples the immune response is a humoral immune response. In other examples the immune response includes both a cellular and humoral immune response. In some examples, a mutant polypeptide is encoded by an oncogene and/or is expressed by a cancer cell. In some examples, a mutant polypeptide is associated with or expressed by a cancer cell. In some examples, the agent is targeted to the cancer cell. In some examples, the agent is a small molecule or antibody.

The targeted therapeutic agents include, but are not limited to, agents that inhibit kinase activity of proteins whose expression (or overexpression) are associated with the development and progression of cancer. Examples of such kinases include Bcr-Abl, Src, Src/Akt, EGFR, PDGFR, Raf, Mek, Erk, PI3K, PDK, AKT, and mTOR. In other examples, the agents act as general inhibitors of these proteins and other protein in their pathway. In some examples, the agents act via direct binding to the active site of the protein and in other cases, the agents cause allosteric changes in the protein as to affect its activity. The compositions described herein are used in combination with these targeted therapeutic agents to control and/or eliminate the escape mutants that develop from the use of these targeted therapeutic agents.

General Techniques

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russell, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual* Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000) and *Vaccines*, S. Plotkin and W. Orenstein, eds., 3$^{rd}$ edition (1999).

Definitions

As used herein, the singular forms "a", "an" and "the" include plural references unless explicitly stated otherwise.

As used herein, "cancer" includes but is not limited to melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, leukemias, and metastatic cancers, thereof.

As used herein, a therapeutic and/or prophylactic "agent" or "drug agent" that is targeted to a cell means that the agent is directed to a molecule(s) associated with or functional for causing the transformation of a cell or supporting tumor progression, in the case of cancer. Examples of therapeutic and/or prophylactic agents that are designed to be targeted to a cell, such as a cancer cell, are disclosed herein and are known in the art.

As used herein, a "mutant polypeptide" encompasses a full length polypeptide encoded within a genome as well as a fragment thereof as long as the fragment comprises a mutation that is known to emerge or has emerged with a specific mutation in response to an agent, such as a prophylactic and/or therapeutic agent. Such mutant polypeptides that emerge with a specific mutation in response to an agent, such as a prophylactic and/or therapeutic agent targeted to a cell, such as a cancer cell, are generally referred to in the art as "escape mutants". Mutant polypeptides are also referred to herein as "mutational escape" as well as "escape mutant." A mutation can be found in any region of a full length polypeptide and may include an amino acid substitution, insertion or deletion or combination thereof, or fusion of non-sequential sequences, such as found in translocation events. In some examples, a mutant polypeptide that is known to emerge or that has emerged with a specific mutation in response to an agent is immunogenic on its own, that is, without being associated with an adjuvant, or other vector or vehicle, such as a yeast vehicle, but this is not required. In other examples, a mutant polypeptide that is known to emerge or that has emerged in response to an agent is immunogenic in association with an adjuvant that promotes its antigenicity.

As used herein, "adjuvants" include, for example, an agonist ligand for a Toll-like receptor (TLR) which elicits cytokine responses of innate immunity, and which are reported to be associated with maturation and activation of antigen presenting cells (APC); CpG nucleotide sequences; single- or double-stranded RNA (TLR7 agonists); lipid moieties, such as lipopolysaccharide (LPS); mannans and glucans, constituents of yeast (which are reported to function through interaction with TLRs 2, 4 and 6); and yeast vehicles, such as those described herein.

Administration of a mutant polypeptide or nucleic acid encoding the mutant polypeptide (which may be produced by any of the methods disclosed herein or known in the art) "in conjunction" with the agent is not intended to mean that the mutant polypeptide and agent are being administered simultaneously, although this is encompassed within the methods disclosed herein. A mutant polypeptide may be administered prior to, concurrently with or after administration of the agent, or a combination of the above. A mutant polypeptide or nucleic acid encoding the mutant polypeptide may be administered hours, days or months after the agent. In some examples, administration of a mutant polypeptide or nucleic acid encoding the mutant polypeptide (which may be produced by any of the methods disclosed herein or known in the art) is prior to administration of the agent, and may additionally be administered after administration of the agent, in particular if the agent is known to interfere directly or indirectly with proliferation of any cell type.

As used herein, a "mimetope" refers to a peptide epitope that is able to mimic the ability of a peptide or polypeptide to elicit an immune response, and in some examples, a cellular and/or humoral immune response, to the target polypeptide or cell expressing the target polypeptide. As used herein a "mimetope" includes, but is not limited to, a peptide that mimics one or more epitopes of a mutant polypeptide protein that is known to emerge or has emerged with a specific mutation in response to administration of a therapeutic and/or prophylactic agent. Such mimetopes can be designed using computer-generated structures of MHC-peptide complexes and putative binding sites with the T cell receptor. Mimetopes can also be obtained by generating random samples of molecules, such as oligonucleotides, peptides or other organic molecules, and screening such samples for their ability to elicit an immune response, such as for example, a cellular immune response, by methods and assays as described herein and known in the art.

As used herein, "ameliorating a symptom of a disease or infection" includes palliating, stabilizing, reversing, slowing or delaying any symptom and/or progression of the disease state, which may be measured by clinical and/or sub-clinical criteria.

In some examples, an "effective amount" of a mutant polypeptide (or mimetope thereof), or nucleic acid encoding the mutant polypeptide refers to an amount capable of eliciting an immune response when administered to a mammal. In some examples, the immune response is a cellular immune response. In other examples the immune response is a humoral response. In some examples the immune response is a cellular and humoral response.

As used herein, "mammal", "mammalian" or "mammalian host" includes human and non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, adult, juvenile, and newborn individuals are intended to be covered, as well as pre-natal mammals.

An "antigen" refers to a molecule containing one or more epitopes (either linear, conformational or both) or immunogenic determinants that will stimulate a host's immune-system, such as a mammal's immune system, to make an antigen-specific humoral and/or cellular antigen-specific response. An antigen may be an "immunogen" by itself or in conjunction with an agent that promotes its antigenicity. The term "antigen" includes whole protein, truncated protein, fragment of a protein, peptide and peptide mimetope. Antigens may be naturally occurring, or genetically engineered variants of the protein. Antigens may be naturally occurring, or genetically engineered variants of the protein. The term "antigen" includes subunit antigens, (i.e., antigens which are separate and discrete from a whole organism with which the antigen is associated in nature). Antibodies such as anti-idiotype antibodies, or fragments thereof, and synthetic peptide mimetopes, that are synthetic peptides which can mimic an antigen or antigenic determinant, are also captured under the definition of antigen as used herein. In some examples, antigen encompasses a mutant polypeptide or is obtainable from a mutant polypeptide that is known to emerge or has emerged with a specific mutation in response to a prophylactic and/or therapeutic agent, and may be naturally occurring or synthetic. An antigen can be as small as a single epitope, or larger, and can include multiple epitopes. As such, the size of an antigen can be as small as about 5-12 amino acids (e.g., a peptide) and as large as a full length protein, including multimers and fusion proteins, chimeric proteins, whole cells, whole microorganisms, or portions thereof (e.g., lysates of whole cells or extracts of microorganisms). It will be appreciated that in some examples (i.e., when the antigen is expressed by a vector, such as a yeast vector, or virus from a recombinant nucleic acid molecule), the antigen includes, but is not limited to a protein, or fragment thereof, fusion protein, chimeric protein, multimers, rather than an entire cell or microorganism.

As used herein, "epitope" is defined herein as a single antigenic site within a given antigen that is sufficient to elicit an immune response, which may be a cellular and/or humoral immune response. Those of skill in the art will recognize that T-cell epitopes are different in size and composition from B-cell epitopes, and that epitopes presented through the Class I major histocompatibility complex (MHC) pathway differ from epitopes presented through the Class II MHC pathway. Generally, a B-cell epitope will include at least about 5 amino acids but can be as small as 3-4 amino acids. A T-cell epitope, such as a cytotoxic T-lymphocyte (CTL) epitope, will include at least about 7-10 amino acids, and a helper T-cell epitope at least about 12-20 amino acids. In this context, the antigen may be a mimetope that is more effective for activating and amplifying T cells capable of recognizing cells expressing the mutated polypeptide. Normally, an epitope whose recognition by T cells will elicit ablation of a target cell will include between about 7 and 15 amino acids, such as, 8, 9, 10, 12 or 15 amino acids.

As used herein, an "immunological response" or "immune response" to a mutant polypeptide (or mimetope thereof) or nucleic acid encoding the polypeptide (or nucleic acid capable of binding to the mutant polypeptide, such as for example, siRNA or antisense RNA), or composition comprising a polypeptide or nucleic acid, includes the development in a mammal of a cellular immune response that recognizes the polypeptide. In some examples, the immune response is a humoral immune response. In some examples, the cellular immune response additionally includes a humoral immune response. The immune response may be specific to the mutant polypeptide, but this is not required. The immune response that is elicited by administration of a mutant polypeptide, or nucleic acid encoding the polypeptide, can be any detectable increase in any facet of the immune response (e.g., cellular response, humoral response, cytokine production), as compared to the immune response in the absence of the administration of the polypeptide or nucleic acid. An immune response may be a mutant polypeptide specific response, but this is not required. Encompassed within the present invention are compositions in association with a mutant polypeptide (or mimetope thereof), or nucleic acid encoding the mutant polypeptide that elicit the immune response.

As used herein, a "humoral immune response" refers to an immune response mediated by antibody molecules or immunoglobulins. Antibody molecules of the present invention include the classes of IgG (as well as subtypes IgG1, IgG2a, and IgG2b), IgM, IgA, IgD, and IgE. Antibodies functionally include antibodies of primary immune response as well as memory antibody responses or serum neutralizing antibodies. With respect to infectious disease, antibodies of the present invention may serve to, but are not required to, neutralize or reduce infectivity of the virus encoding the mutant polypeptide, and/or mediate antibody-complement, or antibody dependent cell cytotoxicity (ADCC) to the mutant polypeptide.

As used herein, a "cellular immune response" is one mediated by T-lymphocytes and/or other white blood cells, including without limitation natural killer (NK) cells and macrophages. T-lymphocytes of the present invention include T-cells expressing alpha/beta T-cell receptor subunits or gamma/delta receptor expressing T-cells and may be either effector or suppressor T-cells.

As used herein, "T-lymphocytes" or "T-cells" are non-antibody producing lymphocytes that constitute a part of the cell-mediated arm of the immune system. T-cells arise from immature lymphocytes that migrate from the bone marrow to the thymus, where they undergo a maturation process under the direction of thymic hormones. Maturing T cells become immunocompetent based on their ability to recognize and bind a specific antigen. Activation of immunocompetent T cells is triggered when an antigen binds to the lymphocyte's surface receptors. It is known that in order to generate T cell responses, antigen must be synthesized within or introduced into cells, subsequently processed into small peptides by the proteasome complex, and translocated into the endoplasmic reticulum/Golgi complex secretory pathway for eventual association with major histocompatibility complex (MHC) class I proteins. Alternatively, peptide antigens may be introduced from the outside of cells to displace peptides already bound into MHC-I or MHC-II receptors. Functionally cellular immunity includes antigen-specific cytotoxic T-lymphocytes cells (CTL).

As used herein, "antigen-specific killer T cells", "CTL", or "cytotoxic T-cells" as used herein refer to cells which have specificity for peptide antigens presented in association with proteins of the MHC or human leukocyte antigens (HLA) as the proteins are referred to in humans. CTLs of the present invention include activated CTL which have become triggered by specific antigen in the context of MHC; and memory CTL or recall CTL to refer to T cells that have become reactivated as a result of re-exposure to antigen as well as cross-reactive or cross clade CTL. CTLs of the present invention include CD4+ and CD8+T cells. Activated antigen-specific CTLs of the present invention promote the destruction and/or lysis of cells of the subject infected with the pathogen to which the CTL are specific, blocking pathogen entry via secretion of chemokines and cytokines including without limitation macrophage inflammatory protein 1 α(MIP-1α), MIP-1β, and RANTES; and secretion of soluble factors that suppress infections. Cellular immunity of the present invention also refers to antigen-specific response produced by the T helper subset of T cells. Helper T cells act to help stimulate the function, and focus the activity of nonspecific effector cells against cells displaying peptide in association with MHC molecules on their surface. A cellular immune response also refers to the production of cytokines, chemokines and other such molecules produced by activated T-cells and/or other white blood cells including those derived from CD4 and CD8 T cells and NK cells. A composition that elicits a cellular immune response may serve to sensitize a mammal by the presentation of the polypeptide in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular polypeptide or antigen to stimulate a cell-mediated immunological response may be determined by a number of assays known in the art, such as by lymphoproliferation (lymphocyte activation) assays, CTL killing assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Other methods of measuring cell-mediated immune responses include measurement of intracellular cytokines or cytokine secretion by T-cell populations, or by measurement of epitope-specific T-cells (e.g., by the tetramer technique) (reviewed by McMichael, A. J., and O'Callaghan, C. A., *J. Exp. Med.* 187(9)1367-1371, 1998; Mcheyzer-Williams, M. G., et al, *Immunol. Rev.* 150:5-21, 1996; Lalvani, A., et al, *J. Exp. Med.* 186:859-865, 1997).

As used herein, an "immunological response", or "immune response" encompasses one which stimulates the production of CTLs, and/or the production or activation of helper T-cells and/or an antibody-mediated immune response. T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors in the context of presentation by MHC/HLA receptors and co receptors.

As used herein, an "immunogenic composition" is a composition that comprises a mutant polypeptide (or including a mimetope of the mutated epitope thereof) or nucleic acid encoding the mutant polypeptide that is known to emerge or has emerged with a specific mutation in response to a therapeutic and/or prophylactic agent, and may or may not comprise an adjuvant that promotes the antigenicity of a mutant polypeptide, wherein administration of the composition to a mammal results in the development of a cellular immune response, a humoral immune response or a cellular and humoral immune response. An immunogenic composition includes a composition that is capable of eliciting a protective cellular immune response, but this is not required.

As used herein, "prophylactic composition" refers to a composition administered to a mammalian subject or host that is "immunologically naïve" or has not been previously exposed to the antigen of the pathogen or one that has not generated an effective immune response to the pathogen to prevent disease, such as cancer and infection or re-infection (however the present invention does not require that the infection or re-infection is completely prevented). Prophylactic compositions of the present invention do not necessarily generate sterilizing immunity in the host or subject to which they have been administered.

As used herein, "therapeutic composition" refers to a composition administered to a subject or host that is subject to cancer, and in some examples, has progressed to a disease state.

As used herein, the term "immunization," "immunize," or "immunized," refers to the process of administering an immunogenic composition to a live mammalian subject or host in an amount effective to induce an immune response to the composition. In some examples, the immune response includes a cellular immune response, e.g., a cytotoxic T cell response. In some examples, the immune response includes a humoral response, e.g. antibody production. In some examples, the immune response includes both a cellular and humoral response.

Yeast-based Compositions and Methods

Provided herein are yeast vectors, yeast vehicles and yeast-based compositions that comprise a mutant polypeptide that is known to emerge or has emerged with a specific mutation in response to an agent. As used herein, the term "yeast vector" and "yeast vehicle" are used interchangeably and include, but are not limited to, whole yeast, a yeast spheroplast, a yeast cytoplast, a yeast ghost, and a subcellular yeast membrane extract or fraction thereof. In some examples, a yeast cell or yeast spheroplast is used to prepare the yeast vehicle, which in some examples comprises nucleic acid molecule encoding the mutant polypeptide, such that the polypeptide is expressed by the yeast cell or yeast spheroplast. In some examples, the yeast vehicle is obtainable from a non-pathogenic yeast. In other examples, the yeast vehicle is obtainable from a yeast selected from the group consisting of: *Saccharomyces, Schizosaccharomyces, Kluveromyces, Hansenula, Candida* and *Pichia*. In some examples, the *Saccharomyces* is *S. cerevisiae*.

In general, the yeast vehicle and mutant polypeptide can be associated by any technique described herein. In some examples, the yeast vehicle is loaded intracellularly with a mutant polypeptide. In other examples, the mutant polypeptide is covalently or non-covalently attached to the yeast vehicle. In yet additional examples, the yeast vehicle and the mutant polypeptide are associated by mixing. In other examples, the mutant polypeptide is expressed recombinantly by the yeast vehicle or by the yeast cell or yeast spheroplast from which the yeast vehicle was derived.

Accordingly, provided herein are yeast vehicles which encompass any yeast cell (e.g., a whole or intact cell) or a derivative thereof that can be used in conjunction with a mutant polypeptide in a composition, or as an adjuvant. The yeast vehicle can therefore include, but is not limited to, a live intact yeast microorganism (i.e., a yeast cell having all its components including a cell wall), a killed (dead) intact yeast microorganism, or derivatives thereof including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), or a subcellular yeast membrane extract or fraction thereof (also referred to previously as a subcellular yeast particle).

Yeast spheroplasts are typically produced by enzymatic digestion of the yeast cell wall. Such a method is described, for example, in Franzusoff et al., *Meth. Enzymol.* 194: 662-674, (1991). Yeast cytoplasts are typically produced by enucleation of yeast cells. Such a method is described, for example, in Coon, *Natl. Cancer Inst. Monogr.* 48: 45-55 (1978). Yeast ghosts are typically produced by resealing a permeabilized or lysed cell and can, but need not, contain at least some of the organelles of that cell. Such a method is described, for example, in Franzusoff et al., *J. Biol. Chem.* 258: 3608-3614 (1983) and Bussey et al., *Biochim. Biophys. Acta* 553: 185-196 (1979). A subcellular yeast membrane extract or fraction thereof refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., *Meth. Enzymol.* 194: 662-674 (1991). One may also use fractions of yeast membrane extracts that contain yeast membrane portions and, when the antigen is expressed recombinantly by the yeast prior to preparation of the yeast membrane extract, the antigen of interest is part of the extract. Yeast can also be electroporated or otherwise loaded with target antigens, such as peptides.

Any yeast strain can be used to produce a yeast vehicle of the present invention. Yeast are unicellular microorganisms that belong to one of three classes: Ascomycetes, Basidiomycetes and Fungi Imperfecti. While pathogenic yeast strains, or nonpathogenic mutants thereof can be used, in some examples, nonpathogenic yeast strains are used. Genera of yeast strains for use in the compositions and methods disclosed herein include *Saccharomyces, Candida* (which can be pathogenic), *Cryptococcus, Hansenula, Kluyveromyces, Pichia, Rhodotorula, Schizosaccharomyces* and *Yarrowia*. In some examples, yeast strains include *Saccharomyces, Candida, Hansenula, Pichia* and *Schizosaccharomyces*. In some examples, a yeast strain is *Saccharomyces*. Species of yeast strains include *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are meant to be included within the aforementioned species. In some examples, yeast species include *S. cerevisiae, C. albicans, H. polymorpha, P. pastoris* and *S. pombe*. In some examples, *S. cerevisiae* is used due to its being relatively easy to manipulate and being "Generally Recognized As Safe" or "GRAS" for use as food additives (GRAS, FDA proposed Rule 62FR18938, Apr. 17, 1997). In some examples, a yeast strain that is capable of replicating plasmids to a particularly high copy number, such as a *S. cerevisiae* cir° strain is used. Other useful strains are known in the art.

In some examples, a yeast vehicle of the present invention is capable of fusing with the cell type to which the yeast vehicle and mutant polypeptide is being delivered, such as a dendritic cell or macrophage, thereby effecting particularly efficient delivery of the yeast vehicle, and in many examples, the antigen, to the cell type. As used herein, fusion of a yeast vehicle with a targeted cell type refers to the ability of the yeast cell membrane, or particle thereof, to fuse with the membrane of the targeted cell type (e.g., dendritic cell or macrophage), leading to syncytia formation. As used herein, a syncytium is a multinucleate mass of protoplasm produced by the merging of cells. It is noted, however, that incorporation of a targeting or fusogenic moiety into the yeast vehicle, while it may be desirable under some circumstances, is not required. It has been shown that yeast vehicles are readily taken up by dendritic cells (as well as other cells, such as macrophages).

Yeast vehicles can be formulated into yeast-based compositions, including compositions intended for direct administration to individuals subject to or at risk for cancer or infection directly or first ex vivo loaded into a carrier such as a dendritic cell, using a number of techniques known to those skilled in the art, prior to administration.

Provided herein are yeast vehicles and compositions comprising them, that comprise at least one mutant polypeptide for administration to a mammal. Also provided are yeast vehicles and compositions comprising them that comprise two or three mutant polypeptides for administration to the animal. This would include yeast-based vaccines that contain mutant polypeptides with one, two, three or more escape mutants to a known or expected targeted or prophylactic agent. In one aspect, the yeast vehicles contain one escape mutation. In other aspects, the yeast vehicles contain two escape mutations. In other aspects, the yeast vehicles contain three escape mutations.

In some examples, the composition comprises one or more of the following:

i). a yeast vehicle comprising nucleic acid which encodes at least one mutant polypeptide, a fragment thereof that comprises a mutation, or a mimetope;

ii). a yeast vehicle comprising at least one mutant polypeptide, a fragment thereof that comprises a mutation, or a mimetope;

iii). a yeast vehicle in association with at least one mutant polypeptide, a fragment thereof that comprises a mutation, or a mimetope;

iv). a yeast vehicle comprising nucleic acid which encodes at least one mutant polypeptide, a fragment thereof that comprises a mutation, or a mimetope loaded intracellularly into a dendritic cell; or v). a yeast vehicle and at least one mutant polypeptide, a fragment thereof that comprises a mutation, or a mimetope loaded intracellularly into a dendritic cell, wherein the mutant polypeptide is known to emerge or has emerged with at least one specific mutation in response to administration of a targeted therapeutic and/or prophylactic agent.

Such compositions can include, one, two, a few, several or a plurality of mutant polypeptides including one or more immunogenic domains of one or more mutant polypeptides, as desired. As used herein, polypeptide includes "antigen." As used herein, an antigen, includes any portion of a protein (peptide, protein fragment, full-length protein), wherein the protein is naturally occurring or synthetically derived, a cellular composition (whole cell, cell lysate or disrupted cells), an organism (whole organism, lysate or disrupted cells), a carbohydrate, a lipid, or other molecule, or a portion thereof, wherein the antigen elicits an antigen-specific immune response (humoral and/or cellular immune response).

Yeast exhibit many of the particulate features of immunostimulatory complexes, with the added advantage that they naturally possess adjuvant-like properties and can be easily engineered to express multiple polypeptides, including antigens. Lu et al., *Cancer Research* 64, 5084-5088 (2004), demonstrated that a yeast-based immunotherapy was capable of eliciting cell-mediated immune responses to tumors expressing Ras oncoproteins harboring a single amino acid mutation. The results demonstrated the ability of yeast vehicles and yeast-based systems to target immunotherapy against polypeptides bearing single amino acid mutations. Accordingly, provided herein are yeast vehicles and yeast-based compositions comprising a mutant polypeptide(s) that is known to emerge or which has emerged in response to an agent, and methods for using them to elicit an immune response to the mutant polypeptide. In some examples, the immune response is a cellular immune response. In some examples, the immune response is a humoral response. In other examples, the immune response is both cellular and humoral. In some further examples, the yeast vehicle is engineered to selectively deliver the antigen to desired cell types. Also provided is a yeast vehicle comprising a yeast strain capable of producing a heterologous precursor protein having a dibasic amino acid processing site. Such a yeast strain is capable of correctly processing the precursor protein into at least one cleavage product protein.

In some examples, the mutant polypeptide is encoded by an oncogene, such as for example, Ras. In some examples the mutant polypeptide is a tumor-associated antigen or a protein expressed by cancer cells.

Preparation of Vectors

Provided herein are compositions comprising a vector, such as a yeast vehicle, in association with a mutant polypeptide. Such association includes expression of the polypeptide by the vector, such as for example, by a recombinant yeast, introduction of a mutant polypeptide into a vector, physical attachment of the mutant polypeptide to the vector, and mixing of the vector and mutant polypeptide together, such as in a buffer or other solution for formulation. Such methods are deemed routine for the skilled artisan.

By way of illustration, a yeast vector is described below. In some examples, a yeast cell used to prepare the yeast vehicle is transformed with a heterologous nucleic acid molecule encoding a mutant polypeptide such that the polypeptide is expressed by the yeast cell. Such a yeast is also referred to herein as a recombinant yeast or a recombinant yeast vehicle. The yeast cell can then be loaded into a dendritic cell as an intact cell, the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen.

According to the present invention, an isolated nucleic acid molecule, or nucleic acid sequence, is a nucleic acid molecule or sequence that has been removed from at least one component with which it is naturally associated. As such, "isolated" does not necessarily reflect the extent to which the nucleic acid molecule has been purified. An isolated nucleic acid molecule useful for transfecting a vector, such as a yeast vehicle, includes DNA, RNA, or derivatives of either DNA or RNA. An isolated nucleic acid molecule can be double stranded or single stranded. An isolated nucleic acid molecule useful in the present invention includes nucleic acid molecules that encode a protein or a fragment thereof, as long as the fragment contains at least one epitope useful in a composition of the present invention.

Nucleic acid molecules can be transformed into a vector, such as a yeast vehicle, by any method known in the art, including, but not limited to, diffusion, active transport, liposome fusion, electroporation, bath sonication, and genetic engineering.

Nucleic acid molecules transformed into yeast vehicles can include nucleic acid sequences encoding one or more mutant polypeptides. Such nucleic acid molecules can comprise partial or entire coding regions, regulatory regions, or combinations thereof. One advantage of yeast strains is their ability to carry a number of nucleic acid molecules and of being capable of producing a number of heterologous proteins. In some examples, a number of antigens to be produced by a yeast vehicle is any number of antigens that can be reasonably produced by a yeast vehicle, and typically ranges from at least one to at least about 5 or more. In one example, about 2 to about 5 antigens are produced by the yeast vehicle.

A mutant polypeptide encoded by a nucleic acid molecule within a yeast vehicle can be a full-length protein, or can be a functionally equivalent protein in which amino acids have been deleted (e.g., a truncated version of the protein), inserted, inverted, substituted and/or derivatized (e.g., acetylated, glycosylated, phosphorylated, tethered by a glycerophosphatidyl inositol (GPI) anchor) such that the modified protein has a biological function substantially similar to that of the natural protein (or which has enhanced or inhibited function as compared to the natural protein, if desired). Modifications can be accomplished by techniques known in the art including, but not limited to, direct modifications to the protein or modifications to the nucleic acid sequence encoding the protein using, for example, classic or recombinant DNA techniques to effect random or targeted mutagenesis.

Expression of mutant polypeptides in vectors is accomplished using techniques known to those skilled in the art. Briefly, a nucleic acid molecule encoding at least one desired mutant polypeptide is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more mutant polypeptides can be on one or more expression vectors operatively linked to one or more transcription control sequences.

In a recombinant molecule of the present invention, nucleic acid molecules are operatively linked to expression vectors containing regulatory sequences such as transcription control sequences, translation control sequences, origins of replication, and other regulatory sequences that are compatible with the vector and that control the expression of nucleic acid molecules. In particular, recombinant molecules of the present invention include nucleic acid molecules that are operatively linked to one or more transcription control sequences. The phrase "operatively linked" refers to linking a nucleic acid molecule to a transcription control sequence in a manner such that the molecule is able to be expressed when transfected (i.e., transformed, transduced or transfected) into a host cell.

Transcription control sequences, which can control the amount of protein produced, include sequences which control the initiation, elongation, and termination of transcription. Particularly important transcription control sequences are those which control transcription initiation, such as promoter and upstream activation sequences. A number of upstream activation sequences (UASs), also referred to as enhancers, are known and can be used in vectors.

Transfection of a nucleic acid molecule into a vector can be accomplished by any method by which a nucleic acid molecule is administered into the cell and includes, but is not limited to, diffusion, active transport, bath sonication, electroporation, microinjection, lipofection, adsorption, and protoplast fusion. Transfected nucleic acid molecules can be integrated into a chromosome or maintained on extrachromosomal vectors using techniques known to those skilled in the art. In the case of yeast, yeast cytoplasts, yeast ghosts, and subcellular yeast membrane extracts or fractions thereof can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplasts, ghosts or subcellular yeast membrane extracts or fractions thereof containing desired antigens.

Effective conditions for the production of recombinant vectors and expression of the mutant polypeptide by the vector include an effective medium in which the vector can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Vectors of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, *Methods in Enzymology*, vol. 194, Academic Press, San Diego).

In one example of the present invention, as an alternative to expression of a mutant polypeptide in a vector, a vector, such as a yeast vehicle is loaded intracellularly with the mutant polypeptide, or peptides or mimetopes that act as epitopes for activating the T cell-mediated immune response against cells bearing the mutated polypeptide. Subsequently, the vector, which now intracellularly contains the epitopes specific for the mutant polypeptide, can be administered to the patient or loaded into a carrier such as a dendritic cell (as described below). With respect to yeast vehicles, mutant polypeptides can be inserted directly into yeast vehicles of the present invention by techniques known to those skilled in the art, such as by diffusion, active transport, liposome fusion, electroporation, phagocytosis, freeze-thaw cycles and bath sonication.

Yeast vehicles that can be directly loaded with a mutant polypeptide or peptides targeting the mutated epitopes include intact yeast, as well as spheroplasts, ghosts or cytoplasts, which can be loaded with antigens after production, but before loading into dendritic cells. Alternatively, intact yeast can be loaded with the antigen, and then spheroplasts, ghosts, cytoplasts, or subcellular particles can be prepared therefrom. Any number of antigens can be loaded into a yeast vehicle, from at least 1, 2, 3, 4 or any whole integer up to hundreds or thousands of antigens, such as would be provided by the loading of a microorganism, by the loading of a mammalian tumor cell, or portions thereof, for example.

In another example, a mutant antigen is physically attached to the vector, such as a yeast vehicle. Physical attachment of the mutant polypeptide to the vector can be accomplished by any method suitable in the art, including covalent and non-covalent association methods which include, but are not limited to, chemically cross-linking the mutant polypeptide to the outer surface of the vector, or biologically linking the mutant polypeptide to the outer surface of the vector, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, in the case of yeast, a chemical can be contacted with the yeast vehicle that alters the charge of the lipid bilayer of yeast membrane or the composition of the cell wall so that the outer surface of the yeast is more likely to fuse or bind to antigens having particular charge characteristics. Targeting agents such as antibodies, binding peptides, soluble receptors, and other ligands may also be incorporated into a mutant antigen as a fusion protein or otherwise associated with an antigen for binding of the antigen to the vector.

In yet another example, the vector and mutant polypeptide are associated with each other by a more passive, non-specific or non-covalent binding mechanism, such as by gently mixing the vector and the antigen together in a buffer or other suitable formulation.

In some examples of the invention, a vector and mutant antigen are both loaded intracellularly into a carrier such as a dendritic cell or macrophage to form an immunogenic composition. A dendritic cell can be any dendritic cell known in the art. Dendritic cells are cells of monocyte and lymphocyte lineages, and are known to be the most potent antigen presenting cell (APC) and to stimulate antigen-specific T cell responses. Mature dendritic cells are typically identified as having the following cell surface marker phenotype: MAC3$^-$, CD80$^+$, CD83$^+$, CD86$^+$, CD401$^\circ$w, CD54$^+$, MHC Class I and MHC Class II, and are capable of FITC-dextran uptake. The dendritic cell used in the composition of the present invention is in some examples, isolated from a patient to which the composition is to be administered (i.e., autologous cells). Dendritic cells can be isolated from the bone marrow or peripheral blood. Such cells can be generated, for example, from peripheral blood monocytes by culture in the presence of granulocyte macrophage colony-stimulating factor, IL-4, and TNF-α, for example. Other methods for isolating and generating dendritic cells are known in the art. (See, for example, Wilson et al., 1999, *Immunol* 162: 3070-8; Romani et al., 1994, *J. Exp Med* 180: 83-93; Caux et al., 1996, *J. Exp Med* 184: 695-706; and Kiertscher et al., 1996, *J. Leukoc. Biol* 59: 208-18).

In order for dendritic cells to efficiently present antigens to native T cells, immature dendritic cells must be activated to mature, as defined by the upregulation of MHC and costimulatory molecules. Yeast provides a powerful activation stimulus to dendritic cells, through Toll-like receptors (TLRs) and phagocytic receptors (see for example, D. M. Underhill and B. Gantner, 2004, *Microbes and Infection* vol. 6: pages 1368-1373; Takeda K. and Akira S., 2005, *International Immunology*, vol. 17: pages 1-14), mannan, glucan and dectin receptors, resulting in upregulation of co-stimulatory immune receptors, MHC molecules, and secretion of immunomodulatory cytokines. Furthermore, when the yeast is preloaded with the antigen before being loaded to the dendritic cells, it provides antigen to dendritic cells in discrete, concentrated packages that are avidly internalized, thereby effectively increasing the amount of antigen available for processing. As will be appreciated by the skilled artisan, additional vectors can be used to load dendritic cells.

Various forms in which the loading of both components can be accomplished are discussed in more detail below. As used herein, the term "loaded" and derivatives thereof refer to the insertion, introduction, or entry of a component (e.g., the yeast vehicle and/or antigen) into a cell (e.g., a dendritic cell). To load a component intracellularly refers to the insertion or introduction of the component to an intracellular compartment of the cell (e.g., through the plasma membrane and at a minimum, into the cytoplasm, a phagosome, a lysosome, or some intracellular space of the cell). To load a component into a cell references any technique by which the component is either forced to enter the cell (e.g., by electroporation) or is placed in an environment (e.g., in contact with or near to a cell) where the component will be substantially likely to enter the cell by some process (e.g., phagocytosis). Loading techniques include, but are not limited to, diffusion, active transport, liposome fusion, electroporation, phagocytosis, and bath sonication. In some examples, passive mechanisms for loading a dendritic cell with the yeast vehicle and/or antigen are used, such passive mechanisms include phagocytosis of the yeast vehicle and/or antigen by the dendritic cell.

In the case of yeast, the yeast vehicle and the mutant polypeptide can be loaded into the dendritic cell at approximately the same time or simultaneously, although it is also possible to load one component into the cell, followed by the other at some period later. In some examples, the yeast vehicle and the mutant polypeptide are associated with one another prior to loading into the dendritic cell. For example, a recombinant yeast vehicle expressing a mutant polypeptide or any other complex or mixture of yeast vehicle and mutant polypeptide can be loaded into a dendritic cell. The dendritic cell may additionally be loaded with free mutant polypeptide, i.e., a polypeptide that is not directly associated with a yeast vehicle when it is introduced (loaded) into the dendritic cell. The addition of free polypeptide with a yeast vehicle-antigen complex can provide an additional enhancement of the immune response against the polypeptide. The free polypeptide(s) loaded into the dendritic cell does not need to be the same as is expressed by the yeast vehicle, loaded into the yeast vehicle, or otherwise associated with the yeast vehicle. In this manner, the immune response against a target cell can be enhanced.

In some examples, a composition comprising the mutant polypeptide or nucleic acid encoding it, comprises one or more adjuvants, including those as described herein, and/or carriers, although this is not required. Adjuvants are typically substances that generally enhance the immune response of an animal to a specific antigen. Suitable adjuvants include, but are not limited to, TLR agonists as described herein, CpG sequences (see for example, Krieg et al. WO 96/02555), single stranded RNA, double stranded RNA, Freund's adjuvant, other bacterial cell wall components (including LPS, flagellin), aluminum-based salts, calcium-based salts, silica, polynucleotides, toxoids, serum proteins, viral coat proteins, other bacterial-derived preparations, gamma interferon, block copolymer adjuvants, such as Hunter's Titermax adjuvant (CytRx™ Inc. Norcross, Ga.), Ribi adjuvants (available from Ribi ImmunoChem Research, Inc., Hamilton, Mont.), and saponins and their derivatives, such as Quil A (available from Superfos Biosector A/S, Denmark).

Carriers are typically compounds that increase the half-life of a therapeutic composition in the treated animal. Suitable carriers include, but are not limited to, polymeric controlled release formulations, biodegradable implants, liposomes, oils, esters, and glycols.

Immunogenic compositions of the present invention may also comprise one or more pharmaceutically acceptable excipients. As used herein, a "pharmaceutically acceptable excipient" refers to any substance suitable for delivering a composition useful in the methods of the present invention to a suitable in vivo or ex vivo site. In some examples, pharmaceutically acceptable excipients are capable of maintaining a vector (or a dendritic cell comprising the vector) in a form that, upon arrival of the vector or cell at a target cell, tissue, or site in the body, the vector (associated with a mutant polypeptide) or the dendritic cell (loaded with a vector and mutant antigen), is capable of eliciting an immune response, including a cellular immune response, a humoral immune response, or both, at the target site (noting that the target site can be systemic). Suitable excipients of the present invention include excipients or formularies that transport, but do not specifically target the composition or vaccine to a site (also referred to herein as non-targeting carriers). Examples of pharmaceutically acceptable excipients include, but are not limited to water, saline, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol.

Cancer

As used herein, cancer includes any type of tumor or neoplasia, including, but not limited to, colorectal cancer, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers thereof. The invention contemplates the leukemias within its definition of "cancer." Chronic myelogenous leukemia is one type of cancer for which this invention has contemplated use in the treatment and prophylaxis.

Examples of specific cancer antigens include, but are not limited to, MAGE (including but not limited to MAGE3, MAGEA6, MAGEA10), NY-ESO-1, gp100, tyrosinase, EGFR, PSA, PSMA, VEG-F, PDGFR, KIT, PMSA, CEA, HER2/neu, Muc-1, hTERT, MART1, TRP-1, TRP-2, Bcr-Abl, and mutant oncogenic forms of p53 (TP53), p73, Ras, Raf, PTENSrc, p38, BRAF, APC (adenomatous polyposis coli), myc, VHL (von Hippel Lindau protein), Rb-1 (retinoblastoma), Rb-2, BRCA1, BRCA2, AR (androgen receptor), Smad4, MDR1 and FLT3.

In some examples, a cancer antigen is, or is obtainable from, a molecule (such as a protein, a peptide, a glycoprotein, or a carbohydrate) that is suitable for targeting by a therapeutic and/or prophylactic agent. Molecular targets for therapeutic and/or prophylactic cancer agents are known in the art, and include, but are not limited to, cell surface receptors (such as receptor tyrosine phosphatases, receptor serine/threonine kinases, and receptor tyrosine kinases), intracellular signaling molecules (such as intracellular tyrosine kinases and other secondary signaling molecules), and transcription factors, cell cycle regulators, proteasome components, proteins involved in angiogenesis, proteins involved in apoptosis control, and chaperone proteins.

Targeting therapeutic and/or prophylactic agents to cancer has been observed to result in the presence of escape mutants, that is, mutant polypeptides. For example, mutations were found in Bcr-Abl that were reported to make individuals previously responsive with treatment of the Bcr-Abl tyrosine kinase inhibitor imatinib (Gleevec) become resistant to the treatment. Gorre et al., *Science*, 293:876-880 (2001); Shah et al., *Cancer Cell*, 2:117-125 (2002); Branford et al., *Blood*, 99(9):3742-3745 (2002); Deininger et al., *Blood*, 105(7):2640-263 (2005). Similarly, mutations in EGFR have also been found in non-small cell lung cancer (NSCLC) patients that make them resistant to gefitinib (Iressa) or erlotinib (Tarceva) treatment. Kobayashi et al., *N. Engl. J. Med.*, 352(8):786-792 (2005). The effectiveness of these anti-cancer agents is therefore significantly limited by the emergence of mutant polypeptides.

Accordingly, provided herein are immunogenic compositions comprising mutant polypeptides encoded by oncogenes and/or expressed by cancer cells or nucleic acid encoding the mutant polypeptides that are known to emerge or which have emerged with a specific mutation in response to administration of a therapeutic and/or prophylactic agent, as well as methods for eliciting an immune response to the mutant polypeptide or cell expressing the mutant polypeptide. In some examples, the immune response is a cellular immune response. In some examples, the immune response is a humoral immune response. In other examples, the immune response includes both cellular and humoral responses.

Polypeptide mutants of cancer antigens can be preexisting in the mammal, i.e., present at the time of the diagnosis, and selectively emerge as a result of administration of the therapeutic and/or prophylactic agent(s). Alternatively, the polypeptide mutants can emerge as a result of the pressure imposed by the agent. The mutation can be located at any amino acid position in the cancer antigen. Although the mutations of polypeptides are described in the context of a single mutation, it is to be understood that the mutant polypeptide can comprise more than one (such as two, three, four, five, or more) amino acid mutations.

In some examples, the polypeptide mutant comprises a mutation besides the junctional region in Bcr-Abl. Bcr-Abl is a constitutively active tyrosine kinase that results from a DNA translocation between chromosome 9 and 22, and thus fusing the Bcr and Abl genes in the Philadelphia chromosome. Bcr- Abl is reported to be causal to the pathogenesis of chronic myeloid leukemia (CML), and its constitutive kinase activity central to its capacity to transform hematopoietic cells in vivo. Imatinib (Gleevec, 2-phenylaminopyrimidine), a tyrosine kinase inhibitor, is a therapeutic agent for CML. Various escape mutations in Bcr-Abl that render the protein resistant to drug therapy (e.g., Gleevec treatment) have been identified in vivo and in vitro. Deininger et al., *Blood,* 105(7): 2640-2653 (2005); Azam et al., *Cell,* 112:831-43 (2003). These mutations are located in various domains of Bcr-Abl, including, but not limited to, the kinase domain (such as the P-loop, the A-loop, T315, the C-helix, the SH3 contact region, or the SH2 contact region), the cap domain, the SH3 domain, the SH2 domain, and other linker regions. In one embodiment, the mutant polypeptide comprises E255K, T315I, and M351T. In other embodiments, the mutant polypeptide comprises T315I. In other embodiments, the mutant polypeptide comprises E255K. In other embodiments, the mutant polypeptide comprises M351T. In still other embodiments, the mutant polypeptide comprises a combination of two of the following: E255K, T315I, and M351T (e.g, E255K/T315I or T315I/M351T or E255K/M351T). In another embodiment, the escape mutant is V299L. In another embodiment, the escape mutant is T315A. In another embodiment, the escape mutant is F317V. In another embodiment, the escape mutant is F311I. For reviews on targeting escape mutants to imanitib (Gleevac), see, for example, Walz et al., *Critical Reviews in Oncology/Hematology* 57:145-164 (2006) and Burgess et al., *The Scientific World JOURNAL,* 6:918-930 (2006).

The cancer antigen may contain one or more mutations at different amino acid positions. For Bcr-Abl and its response to imatinib (Gleevec) treatment, various escape mutations have been described in the art. In one aspect, the mutation is a T315I escape mutation. In another aspect, the mutation is an E255K mutation. In yet another aspect, the mutation is a M351T mutation. In other aspects, the mutations are a combination of all three E255K, T315I and M351T. In other aspects, the mutations are a combination of two of the three mutations disclosed above (e.g, E255K/T315I or T315I/M351T or E255K/M351T). The cancer antigen may further contain other mutations, such as mutations associated with transforming events.

In some examples, a polypeptide mutant can be a fusion polypeptide that contains multiple immunogenic domains from one or more mutant polypeptides of cancer antigens. For example, it is known that there are several different mutations in the Bcr-Abl protein that emerge as escape mutations even with administration of Gleevec (e.g., E255K, T315I, M351T, V299L, T315A, F317V, or F311I). A mutant polypeptide may comprise one or more Bcr-Abl mutations at the same position and/or different positions and/or combinations of mutations at more than one position.

Thus, in one aspect, the invention provides for a method for targeting the ablation of a mutational escape in an individual in need thereof by administering to the individual an effective amount of a targeted therapeutic agent and a composition comprising one or more of the following: i) a yeast vehicle comprising nucleic acid which encodes at least one mutant polypeptide associated with cancer, a fragment thereof that comprises a mutation, or a mimetope; ii) a yeast vehicle comprising at least one mutant polypeptide associated with cancer, a fragment thereof that comprises a mutation, or a mimetope; iii) a yeast vehicle in association with at least one mutant polypeptide associated with cancer, a fragment thereof that comprises a mutation, or a mimetope; iv) a yeast vehicle comprising nucleic acid which encodes at least one mutant polypeptide associated with cancer, a fragment thereof that comprises a mutation, or a mimetope loaded intracellularly into a dendritic cell; or v) a yeast vehicle and at least one mutant polypeptide associated with cancer, a fragment thereof that comprises a mutation, or a mimetope loaded intracellularly into a dendritic cell, wherein the mutant polypeptide is known to emerge or has emerged with at least one specific mutation in response to administration of a targeted therapeutic and/or prophylactic agent for cancer.

The targeted therapeutic agent can be any type of cancer that is used for prophylaxis or treatment of cancer. Non-limiting examples for the agent are: a tyrosine kinase inhibitor, a Src kinase inhibitor, a dual Src/Abl inhibitors, an agent that acts on the Ras/Raf/Mek pathway, an agent that acts in the PI3K pathway; an agent that acts on chaperone proteins that are involved in oncogenic signal transduction pathways. The combination of the therapeutic agent and the targeted ablation methodology is effective for the elimination of cells that contain the escape mutation. Many of the existing therapeutic agents do not eliminate cells with escape mutations while they may eliminate the wild-type phenotype. As such, the agent alone or the targeted ablation methodology alone is not as effective when used by themselves as when they are used in combination with each other.

Non-limiting examples of targeted therapeutic agents that act as tyrosine kinase inhibitors are: imatinib, nilotinib, PD1866326, PD180970, AP23464, BMS-354825, ON012380, VX-680, and BIRB-796.

Non-limiting examples of targeted therapeutic agents that act as Src kinase inhibitors are PD166326, PD180970, AP23464, BMS-354825, AZM475271, PP1, PP2, AP-23236, CGP76030, and PD173955.

Non-limiting examples of targeted therapeutic agents that affects the stability of proteins that are involved in cancer (e.g., Bcr-Abl) include heat shock proteins or other chaperone proteins that associate with the protein that is involved in cancer. In some aspects, the agent is geldanamycin/17-AAG or NVP-LAQ824.

The targeted therapeutic agent can also act in a signaling pathway that is downstream of Bcr-Abl. Examples of signaling pathways that are contemplated within the scope of this invention include, but are not limited to, Ras, Raf, Mek, Erk, Src, PI3K, PDK, ASK, mTOR. Non-limiting examples of agents that target the aforementioned signaling pathways include: SCH66336, BAY-439006, CI-1040, LY294002, wortmanin, OSU-03012, CCI-779, R115777, BMS-214662, U0126, PD184352, rapamycin, RAD001, CCI-779, and AP23573. In addition, agents that target protein associated with the activation of these pathways are also contemplated within the scope of the invention. For example, farnesyl transferase inhibitors such as SCH66336, R115777, and BMS-214662, can be used in combination with the targeted ablation methodology described herein.

In addition to the targeting of proteins such as Bcr-Abl, other cancer therapeutics are directed to other targets such as FLT3, PDGFR, VEGR, PKC, and c-Kit, as discussed in greater detail below. In some embodiments, D816V and V560G are escape mutations in c-Kit that can be targeted by the methodologies described herein. The use of targeted ablation to mutational escape can also be used in combination with agents directed to the aforementioned targets and any other cancer antigen and/or proteins associated with cancer. For example, PKC412 and sunitinib (SU11248) can be used for targeting FLT3, PDGFR, VEGR, PKC, and c-Kit. Targeted ablation to mutational escape can also be used in combination with agents to treat other cancers, such as imatinib-resistant hypoeosiniphilic symdrome (HES) or gastrointestinal stromal tumor (GIST).

In some examples, the mutant polypeptide comprises a mutation in EGFR. EGFR is a receptor tyrosine kinase that plays a key role in the initiation of cell division in both normal and cancer cells. In a number of cancers, including non-small cell lung cancer (NSCLC) and glioblastoma (brain cancer), it is reported that EGFR is either overexpressed or mutated, and these changes are believed to be associated with the formation and growth of tumors. Two oral anilinoquinazoline EGFR tyrosine kinase inhibitors, gefitinib (Iressa) and erlotinib (Tarceva), have been approved in the United States for treatment of NSCLC. An escape mutation, T790M, was found in EGFR that is reported to render the mammalian subject resistant to treatment of Iressa or Tarceva. As such, the use of targeted ablation to mutational escape can also be used in combination with Iressa or alternatively, with Tarceva to treat individuals who have developed escape mutations to these agents.

Accordingly, provided herein are compositions comprising a mutant polypeptide of EGFR (or mimetope thereof) or nucleic acid encoding EGFR and methods for their use in eliciting an immune response. In some examples, the immune response is a cellular immune response. In some examples, the immune response is a humoral immune response. In other examples, the immune response includes both a cellular and humoral immune response. In some examples, the mutant polypeptide comprises a mutation in the kinase domain of EGFR.

In some examples, the mutant polypeptide comprises a mutation in platelet-derived growth factor receptor (PDGFR). PDGFR is a receptor tyrosine kinase. Activation of PDGFR is reported to be critical for the progression of various types of cancers such as glioblastoma, dermatofibrosarcoma protuberans, and CML. Accordingly, provided herein are compositions comprising a mutant polypeptide of PDGFR (or mimetope thereof) or nucleic acid encoding PDGFR and methods for their use in eliciting an immune response. In some examples, the immune response is a cellular immune response. In some examples, the immune response is a humoral immune response. In other examples, the immune response includes both a cellular and humoral immune response. In some examples, the mutant polypeptide comprises a mutation in the kinase domain of PDGFR.

In some embodiments, the mutant polypeptide comprises a mutation of KIT. KIT is a tyrosine kinase receptor for stem-cell factor (SCF). Activation of KIT by mutations in the kinase domain is reported to be associated with gastrointestinal stromal tumor (GIST) and other types of tumors. Frequent escape mutations, such as D816V or V560G, in c-kit have been described in patients treated with Gleevec. See, for example, Walz et al., *Critical Reviews in Oncology/Hematology*, 57:145-164 (2006). Accordingly, provided herein are compositions comprising a mutant polypeptide of KIT (or mimetope thereof) or nucleic acid encoding KIT and methods for their use in eliciting an immune response. In some examples, the immune response is a cellular immune response. In some examples, the immune response is a humoral immune response. In other examples, the immune response includes both a cellular and humoral immune response. In some examples, the mutant polypeptide comprises a mutation in the kinase domain of KIT. In some examples, the mutant polypeptide comprises the T670I mutation with respect to the wild-type KIT polypeptide.

Accordingly, provided herein are compositions comprising such mutant polypeptides (or mimetopes thereof) or nucleic acid encoding the mutant polypeptides and methods for their use in eliciting an immune response. In some examples, the immune response is a cellular immune response. In some examples, the immune response is a humoral immune response. In other examples, the immune response includes both a cellular and humoral immune response. In some examples, a mutant polypeptide that is known to emerge or that has emerged with a specific mutation in response to an agent is immunogenic on its own, that is, without being associated with an adjuvant but this is not required. In other examples, a mutant polypeptide that is known to emerge or that has emerged in response to an agent is immunogenic in association with an adjuvant, such as a Toll-like receptor ligand or agonist, or CpG nucleotide sequence, or other vector or vehicle, such as a yeast vehicle, that promotes its antigenicity.

Accordingly, the compositions described herein are used for eliciting an immune response to a mutant polypeptide in a mammal, comprising administration to the mammal of an effective amount of the composition in conjunction with the targeted therapeutic and/or prophylactic agent. In some examples, the composition comprises one or more of the following:

i). a yeast vehicle comprising nucleic acid which encodes at least one mutant polypeptide, a fragment thereof that comprises a mutation, or a mimetope;

ii). a yeast vehicle comprising at least one mutant polypeptide, a fragment thereof that comprises a mutation, or a mimetope;

iii). a yeast vehicle in association with at least one mutant polypeptide, a fragment thereof that comprises a mutation, or a mimetope;

iv). a yeast vehicle comprising nucleic acid which encodes at least one mutant polypeptide, a fragment thereof that comprises a mutation, or a mimetope loaded intracellularly into a dendritic cell; or v). a yeast vehicle and at least one mutant polypeptide, a fragment thereof that comprises a mutation, or a mimetope loaded intracellularly into a dendritic cell, wherein the mutant polypeptide is known to emerge or has emerged with at least one specific mutation in response to administration of a targeted therapeutic and/or prophylactic agent.

Further the compositions may be used in preparation of or manufacture of medicaments for eliciting an immune response to a mutant polypeptide in a mammal in conjunction with a targeted therapeutic and/or prophylactic agent. In some examples, the mutant polypeptide is an oncogene, a tumor-associated antigen or a polypeptide expressed by a cancer cell. In some examples the cancer cell is selected from the group consisting of colorectal cancer, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers.

In some examples the immune response is a cellular immune response. In other examples the immune response is a humoral immune response. In yet other examples the immune response includes both a cellular and humoral immune response.

In addition, the compositions described herein are used to treat a disease in a mammal, comprising administration to the mammal of an effective amount of the composition, wherein the disease is associated with a mutant polypeptide that is known to emerge or has emerged with at least one specific mutation in response to administration of a targeted therapeutic and/or prophylactic agent. In some examples the compositions are used in conjunction with the targeted therapeutic and/or prophylactic agent. Further, the compositions may be used in preparation or manufacture of medicaments for treating the disease in a mammal in conjunction with a targeted therapeutic and/or prophylactic agent. In some examples, the mutant polypeptide, is an oncogene, a tumor-associated antigen or a polypeptide expressed by a cancer cell. In some examples the cancer cell is selected from the group consisting of colorectal cancer, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias and metastatic cancers. In some examples the disease is cancer.

Methods of identifying new mutant polypeptides in a cancer antigen that emerge as a result of administration of agents are known in the art. Escape mutations identified by in vitro methods have shown a high degree of correlation with those that develop in vivo. See, for example, Azam et al, *Cell*, 112:831-843 (2003); Cools et al., *Cancer* Research, 64:6385-6389 (2004); Blencke et al., *Chem. Biol.*, 11:691-701 (2004). For example, Azam et al. provided a screening method for identifying resistant mutant polypeptides to target-directed anti-cancer agents, which is generally applicable to any agent-mutant polypeptide pair (Azam et al., *Biol. Proced. Online*, 5(1):204-210 (2003)). Briefly, the cDNA encoding the target mutant polypeptide is cloned in a cloning vector and subjected to random mutagenesis, rendering a library of mutations in the target cancer polypeptide. The library is then introduced into cells susceptible to treatment with the agent. Colonies that are resistant to treatment with the agent are then selected in the presence of the therapeutic agent, isolated, and sequenced to reveal the putative mutations. To validate the resistant phenotype of each candidate mutation, mutations can also be created in the native cDNA de novo by site-directed mutagenesis. The mutant cDNAs are introduced into drug-sensitive cells to confirm their drug-resistant phenotypes. Drug resistance can further be confirmed by cell proliferation assays. Mutations can also be analyzed for their structural consequences by mapping into a model of the protein crystal structure.

Compositions and Pharmaceutical Formulations and Administration Thereof

Provided herein are compositions comprising vectors in association with a mutant polypeptide, including compositions to be administered to a patient directly or first loaded into a carrier such as a dendritic cell, using a number of techniques known to those skilled in the art. For example, vectors can be dried by lyophilization or frozen by exposure to liquid nitrogen or dry ice. Compositions comprising yeast vehicles can also be prepared by packing yeast in a cake or a tablet, such as is done for yeast used in baking or brewing operations. In addition, prior to loading into a dendritic cell, or other type of administration, vectors can also be mixed with a pharmaceutically acceptable excipient, such as an isotonic buffer that is tolerated by the host cell. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as polyethylene glycols (PEG) sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

Provided herein are methods comprising administering a composition (such as an immunogenic composition) that comprises a vector in association with a mutant antigen to a mammal at risk for cancer or infection or subject to cancer or infection. The methods are generally useful for eliciting an immune response, which in some examples, is an cellular immune response in the mammal. Such methods are believed to be useful in eliciting a cellular immune response to a mutant polypeptide that has emerged in response to an agent (s) or is believed will emerge in response to an agent; thereby minimizing or reversing resistance to the agent, and/or extending the efficacy of the agent and/or minimizing, reducing or reversing some symptoms of disease or infection.

Accordingly, provided herein are methods for minimizing resistance to a prophylactic and/or therapeutic agent in a mammal, comprising administering to the mammal a effective amount of a composition comprising a vector, such as for example, a yeast vehicle, in association with a mutant polypeptide that has emerged in response to the agent. Also, provided herein are methods for reducing resistance to an agent administered to a mammal at risk of disease or infection or subject to disease or infection, whether the agent is administered prophylactically and/or therapeutically, comprising administering to the mammal an effective amount of a composition in conjunction with the agent, wherein said composition comprises, a. a cell, vector or virus comprising nucleic acid that encodes the mutant polypeptide;

b. a cell, vector or virus in association with the mutant polypeptide;

c. the mutant polypeptide, or a peptide (mimetope) that elicits an immune response to the mutant polypeptide; or d. nucleic acid encoding the mutant polypeptide, or nucleic acid, such as siRNA or anti-sense RNA that binds the nucleic acid, wherein an effective amount of the composition is administered in conjunction with the agent.

In some examples, the composition comprises one or more of the following:

i). a yeast vehicle comprising nucleic acid which encodes at least one mutant polypeptide, a fragment thereof that comprises a mutation, or a mimetope;

ii). a yeast vehicle comprising at least one mutant polypeptide, a fragment thereof that comprises a mutation, or a mimetope;

iii). a yeast vehicle in association with at least one mutant polypeptide, a fragment thereof that comprises a mutation, or a mimetope;

iv). a yeast vehicle comprising nucleic acid which encodes at least one mutant polypeptide, a fragment thereof that comprises a mutation, or a mimetope loaded intracellularly into a dendritic cell; or v). a yeast vehicle and at least one mutant polypeptide, a fragment thereof that comprises a mutation, or a mimetope loaded intracellularly into a dendritic cell, wherein the mutant polypeptide is known to emerge or has emerged with at least one specific mutation in response to administration of a targeted therapeutic and/or prophylactic agent.

In some examples, the composition is capable of eliciting a cellular immune response. In other examples, the immune response is a humoral immune response. In other examples, the immune response includes both a cellular and humoral immune response.

In some examples of the methods, the composition comprises an adjuvant. In yet other examples, the composition further comprises an agonist or ligand for a Toll-like receptor or a phagocytic receptor or both. In other examples, the composition comprises a yeast vehicle. In yet other examples, the composition comprises a CpG sequence. In other examples, the cell is a dendritic cell. In some examples, the mammal is a human.

Also provided herein are vectors, including for example, yeast vehicles, viruses and compositions, such as, for example, yeast-based compositions comprising yeast vehicles, including immunogenic compositions, for use in methods for eliciting a mutant polypeptide specific immune response in a mammal that has been, will be, or is being administered the agent(s). In some examples, the mammal is at risk for a disease, and a vector associated with a mutant polypeptide, a fragment thereof that comprises a mutation or a mimetope, and/or compositions comprising such vector, is administered prophylactically, before, concurrently with and/or after the agent. In other examples, the mammal is subject to disease and a vector associated with a mutant polypeptide, and/or compositions comprising such vectors, is administered therapeutically, before, concurrently with and/or after the agent. Administration of such yeast vehicles in association with a mutant polypeptide may be used, for example, to increase susceptibility of the mammal to a therapeutic and/or prophylactic agent; and/or to increase therapeutic efficacy of such agents; and/or to extend the effective life cycle of such agents. In some examples, a mutant polypeptide is identified prior to administration of a vector or composition as described herein, and in other examples, a mutant polypeptide is predicted to occur in response to an agent.

Compositions described herein that comprise vectors, such as yeast vehicles, in association with a mutant polypeptide, a fragment thereof that comprises a mutation or a mimetope, and the therapeutic or prophylactic agent can be administered either simultaneously or sequentially, whether prior to or after administration of the agent(s). Simultaneous administration encompasses administration together in one composition or alternatively, as separate compositions. In some examples, the agent and mutant polypeptide, or nucleic acid encoding it, are in different formulations and are administered simultaneously and separately. As will be appreciated, in some examples, wherein the agent and mutant polypeptide, or nucleic acid encoding it, are administered sequentially, the administration may be on a daily, weekly, or monthly basis as will be deemed appropriate by the practitioner for the mammal. The term "simultaneous administration" as used herein, means that the composition comprising the yeast vehicle and the therapeutic agent are administered on the same day. Either the composition comprising the mutant polypeptide or the therapeutic agent may be administered first. When administered simultaneously, the composition comprising the yeast vehicle and the therapeutic agent may be contained in the same dosage (i.e., a unit dosage comprising both the composition comprising the yeast vehicle and the therapeutic agent) or in discrete dosages (e.g., the composition comprising the yeast vehicle is contained in one dosage form and the therapeutic agent is contained in another dosage form).

In some examples, the composition comprising the mutant polypeptide is administered as a "follow-up treatment," i.e., after treatment of the agent has been initiated or after an increase in a symptom of disease is observed. However, the composition comprising the vector, such as a yeast vehicle, can also be administered before treatment with the therapeutic or prophylactic agent has been initiated.

The methods described herein may also comprise administering a vector and a mutant polypeptide to a mammal, wherein the vector and the polypeptide are not complexed with each other, i.e., the polypeptide is not recombinantly expressed by the vector, loaded into the vector, or physically attached to the vector. The vector and the mutant polypeptide can be mixed in a formulation prior to administration to the subject, or administered separately. The administration process can be performed ex vivo, such as by introduction by dendritic cells loaded with the yeast vehicle, or in vivo. Ex vivo administration refers to performing part of the regulatory step outside of the mammal, such as administering a composition of the present invention to a population of cells (dendritic cells) removed from a mammal under conditions such that the vector and mutant polypeptide are loaded into the cell, and returning the cells to the mammal. The composition comprising a vector can then be returned to a mammal, or administered to a mammal, by any suitable mode of administration.

Administration of a composition, including a composition comprising a dendritic cell loaded with a vector and mutant polypeptide, can be, for example, systemic, or mucosal. The routes of administration will be apparent to those of skill in the art, depending on the type of condition, the mutant polypeptide used, and/or the target cell population or tissue. Methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. Routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., Proc. Natl. Acad. Sci. USA 189: 11277-11281 (1992). For example, in one example, a composition comprising a yeast vehicle can be formulated into a composition suitable for nebulized delivery using a suitable inhalation device or nebulizer. Oral delivery can include solids and liquids that can be taken through the mouth, and is useful in the development of mucosal immunity and since compositions comprising yeast vehicles can be easily prepared for oral delivery, for example, as tablets or capsules, as well as being formulated into food and beverage products. Other routes of administration that modulate mucosal immunity are useful in the treatment of cancer or infectious disease. Such routes include bronchial, intradermal, intramuscular, intranasal, other inhalatory, rectal, subcutaneous, topical, transdermal, vaginal and urethral routes. The route of delivery is any route of delivery of a composition comprising a yeast vehicle to the respiratory system, including, but not limited to, inhalation, intranasal, intratracheal, and the like.

Effective administration of a cell, vector, such as a yeast vehicle, or virus, or composition comprising a cell, vector, virus or yeast vehicle as described herein to a mammal at risk for or subject to disease does not require that the mammal is protected from the disease. Effective dose parameters can be determined using methods standard in the art that are suitable to minimize or reduce symptoms of disease, or minimize progression of the disease. Such methods include, for example, determination of survival rates, side effects (i.e., toxicity) and progression or regression of disease.

For use with a yeast vehicle, a suitable single dose size is a dose that is capable of eliciting an immune response in a mammal, in some examples, a cellular immune response, which may be an antigen-specific immune response, when administered one or more times over a suitable time period. As will be understood by the skilled artisan, the dose of the composition required to elicit an immune response depends on a number of factors. One of skill in the art can readily determine appropriate single dose sizes for administration based on the size of the mammal and the route of administration.

A suitable single dose of a composition comprising a vector in association with a mutant polypeptide is a dose that is capable of effectively providing a vector and/or mutant polypeptide to a given cell type, tissue, or region of the patient body in an amount effective to elicit an immune response, when administered one or more times over a suitable time period. In the case of yeast, a single dose of a yeast vehicle of the present invention is from about 0.004 YU ($4 \times 10^3$ cells) to about 100 YU ($1 \times 10^9$ cells), such as 0.1 YU ($1 \times 10^6$ cells) to about 100 YU ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$, etc.). In one embodiment, 2 YU ($2 \times 10^7$ yeast) are used. This range of doses can be effectively used in any organism of any size, including mice, monkeys, humans, etc. When the composition is administered by loading the yeast vehicle and mutant antigen into dendritic cells, a single dose of a composition described herein is from about $0.5 \times 10^6$ to about $40 \times 10^6$ dendritic cells per mammal per administration. In other examples, a single dose is from about $1 \times 10^6$ to about $20 \times 10^6$ dendritic cells per individual, and yet other examples from about $1 \times 10^6$ to about $10 \times 10^6$ dendritic cells per mammal. A "boost" dose of a composition comprising a yeast vehicle as described herein may be administered when the immune response against the mutant antigen has waned, or as needed to provide an immune response or induce a memory response against a particular mutant polypeptide. Boost doses can be administered from about 1 week to several years after the original administration. In one example, an administration schedule is one in which from about $1 \times 10^5$ to about $1 \times 10^9$ yeast cell equivalents of a composition is administered weekly for 3 months, to weekly for 1 month (5 doses) followed by monthly administration.

In some examples, a dendritic cell composition comprising a yeast vehicle as described herein contains from about $0.5 \times 10^6$ to about $40 \times 10^6$ dendritic cells per single dose per patient, and in another example, from about $1 \times 10^6$ to about $10 \times 10^6$ dendritic cells per single dose per patient. These doses are given for a typical human or other primate. Doses suitable for other animals can be determined by those of skill in the art. For example, for a mouse, a suitable dose is from about $1 \times 10^6$ to about $3 \times 10^6$ per single dose per mouse. Other doses can be determined by the skilled artisan and is well within the ability of those of skill in the art. A composition effective to administer to a mammal contains from about $0.5 \times 10^6$ to about $40 \times 10^6$ dendritic cells per single dose per individual mammal.

It will be obvious to one of skill in the art that the number of doses administered to a mammal is dependent upon the nature of the yeast vehicle and the response of a mammal to the administration. Thus, it is within the scope of the present invention that a suitable number of doses include any number required for the desired purpose. For example, repeated dosing may increase the number of T cells available to attack target cells. The dosage and frequency of the administration may be adjusted during the course of the administration as will be apparent to the skilled.

One of skill in the art can also monitor the effects of the dosing by using animal models, such as mouse models of leukemia. Such mouse models are readily known to one of the skill in the art. One method of monitoring the effect of dosing is to monitor the survival rate of the mice (vaccinated and unvaccinated) after a challenge or a boost. Another method of monitoring the effect of dosing is to measure the percentage of leukemic cells over time. Some mouse models exist whereby leukemic cells are tagged with a marker, such a green fluorescent protein (GFP). The GFP-positive cells indicate leukemic cells and can be monitored in various compartments of the body, such as bone marrow.

Kits

Provided herein are kits for carrying out any of the methods described herein. Kits of the invention may comprise at least one yeast vehicle and at least one mutant polypeptide associated with cancer that is known to emerge or has emerged with a specific mutation in response to administration of a targeted therapeutic and/or prophylactic drug agent(s). The kit may further comprise a therapeutic and/or prophylactic drug agent. In some examples, the drug agent is targeted to cancer cells. Exemplary agents include, but are not limited to, imatinib, nilotinib, PD166326, PD180970, AP23464, BMS-354825, ON012380, VX-680, BIRB-796, AZM475271, PP1, PP2, AP-23236, CGP76030, PD173955, Geldanamycin/17-AAG, NVP-LAQ824, SCH66336, BAY-439006, CI-1040, LY294002, wortmannin, OSU-03012, CCI-779, R115777, BMS-214662, U0126, PD184352, rapamycin, RAD001, CCI-779, AP23573, PKC412 or SU11248. The kit may further comprise instructions for carrying out a method described herein.

Kits comprising a single component will generally have the component enclosed in a container (e.g., a vial, ampoule, or other suitable storage container). Likewise, kits including more than one component may also have the reagents in containers (separately or in a mixture).

The instructions relating to the use of the kit for carrying out the invention generally describe how the contents of the kit are used to carry out the methods of the invention. Instructions supplied in the kits of the invention are typically written instructions on a label or package insert (e.g., a paper sheet included in the kit), but machine-readable instructions (e.g., instructions carried on a magnetic or optical storage disk) are also acceptable.

Although the foregoing invention has been described in some detail by way of illustration and example for purposes of clarity of understanding, it will be apparent to those skilled in the art that certain changes and modifications may be practiced. Therefore, the descriptions and examples should not be construed as limiting the scope of the invention.

EXAMPLES

Example 1

Construction of Yeast Vehicles Comprising Escape Mutations

The purpose of this example to describe yeast constructs which contain escape mutants known to occur with the administration of Gleevec.

Yeast-based vectors expressing about 400 amino acids of the Abl portion from p210 Bcr-Abl were made. These vectors were under the control of a constitutive TEF2 promoter (Transcription Elongation Factor 2). The yeast containing the following constructs were cultured, harvested, washed with PBS, heat killed at 56 degrees C. for 1 hour, washed again with PBS and then resuspended in PBS for administration to the mice.

The following sequences were used to generate various yeast constructs:

Construct #1 VK13-BA5M-VAX E1.E2.E3

```
                                                  (SEQ ID NO: 1)
MADEAPNLFVALYDFVASGDNTLSITKGEKLRVLGYNHNGEWCEAQTKNG        50

QGWVPSNYITPVNSLEKHSWYHGPVSRNAAEYLLSSGINGSFLVRESESS       100

PGQRSISLRYEGRVYHYRINTASDGKLYVSSESRFNTLAELVHHHSTVAD       150

GLITTLHYPAPKRNKPTIYGVSPNYDKWEMERTDITMKHKLGGGQYGKVY       200

EGVWKKYSLTVAVKTLKEDTMEVEEFLKEAAVMKEIKHPNLVQLLGVCTR       250

EPPFYIIEFMTYGNLLDYLRECNRQEVSAVVLLYMATQISSATEYLEKK        300

NFIHRDLAARNCLVGENHLVKVADFGLSRLMTGDHHHHHH*
```

This construct contains three escape mutants: E255K, T315I, and M351T. This sequence was changed at V227I and N336S, which corresponds to a change from the human residues to residues that would correspond with mouse residues. The MADEAP sequence at the beginning has been added to the Bcr-Abl sequence for stability of yeast expression. The bolded, underlined text shows mutations corresponding to escape mutants (E255K, T315I, and M351T). The last 6 residues are a hexahistidine tag. The 328 amino acids in between the MADEAP sequence and the hexahistidine tag are from the human Abl kinase domain. The final amino acid is a stop codon (*).

Construct #2 VK14-VAX E2 Only

```
                                                  (SEQ ID NO: 2)
MADEAPNLFVALYDFVASGDNTLSITKGEKLRVLGYNHNGEWCEAQTKNG        50

QGWVPSNYITPVNSLEKHSWYHGPVSRNAAEYLLSSGINGSFLVRESESS       100

PGQRSISLRYEGRVYHYRINTASDGKLYVSSESRFNTLAELVHHHSTVAD       150

GLITTLHYPAPKRNKPTIYGVSPNYDKWEMERTDITMKHKLGGGQYGEVY       200

EGVWKKYSLTVAVKTLKEDTMEVEEFLKEAAVMKEIKHPNLVQLLGVCTR       250

EPPFYIIEFMTYGNLLDYLRECNRQEVSAVVLLYMATQISSAMEYLEKK        300

NFIHRDLAARNCLVGENHLVKVADFGLSRLMTGDHHHHHH*
```

This construct contains only one escape mutant: T315I. This sequence was changed at V227I and N336S, which corresponds to a change from the human residues to residues that would correspond with mouse residues. The MADEAP sequence at the beginning has been added to the Bcr-Abl sequence for stability of yeast expression. The bolded and underlined text shows mutations corresponding to escape mutant (T315I). The last 6 residues are a hexahistidine tag. The sequence in between the MADEAP sequence and the hexahistidine tag are from the human Abl kinase domain. The final amino acid is a stop codon (*).

Construct #3 VK15-JCN-BAM-VAX b3a2

(SEQ ID NO: 3)

```
MADEAPCFRSFSLTSVEQQMLTNSCVKLQTVHHIPLTINKEDDESPGLYG         50

FLHVIVHSATGFKQSSKALQRPVASDFEPQGLSEAARWNSKENLLAGPSE        100

NDPNLFVALYDFVASGDNTLSITKGEKLRVLGYNHNGEWCEAQTKNGQGW        150

VPSNYITPVNSLEKHSWYHGPVSRNAAEYLLSSGINGSFLVRESESSPGQ        200

RSISLRYEGRVYHYRINTASDGKLYVSSESRFNTLAELVHHHSTVADGLI        250

TTLHYPAPKRNKPTIYGVSPNYDKWEMERTDITMKHKLGGGQYGEVYEGV        300

WKKYSLTVAVKTLKEDTMEVEEFLKEAAVMKEIKHPNLVQLLGVCTREPP        350

FYIITEFMTYGNLLDYLRECNRQEVSAVVLLYMATQISSAMEYLEKKNFI        400

HRDLAARNCLVGENHLVKVADFGLSRLMTGDHHHHHH*
```

This construct is the wild type Bcr-Abl with mouse resides at the junction of Bcr and Abl. This sequence was changed at V227I and N336S and two changes to residues upstream of human Bcr-Abl junction that were replaced with corresponding mouse amino acids, which corresponds to a change from the human residues to residues that would correspond with mouse residues (these changes are indicated above in bold and with double underline). The MADEAP sequence at the beginning has been added to the Bcr-Abl sequence for stability of yeast expression. The last 6 residues are a hexahistidine tag. The sequence in between the MADEAP sequence and the hexahistidine tag are from human Bcr-Abl kinase containing 97 residues upstream of Bcr-Abl junction. The final amino acid is a stop codon (*).

Construct #4 Fully Human E2 Only (SEQ ID NO: 4)

```
MADEAPNLFVALYDFVASGDNTLSITKGEKLRVLGYNHNGEWCEAQTKNG         50

QGWVPSNYITPVNSLEKHSWYHGPVSRNAAEYLLSSGINGSFLVRESESS        100

PGQRSISLRYEGRVYHYRINTASDGKLYVSSESRFNTLAELVHHHSTVAD        150

GLVTTLHYPAPKRNKPTIYGVSPNYDKWEMERTDITMKHKLGGGQYGEVY        200

EGVWKKYSLTVAVKTLKEDTMEVEEFLKEAAVMKEIKHPNLVQLLGVCTR        250

EPPFYIITEFMTYGNLLDYLRECNRQEVNAVVLLYMATQISSAMEYLEKK        300

NFIHRDLAARNCLVGENHLVKVADFGLSRLMTGDHHHHHH*
```

This construct contains fully human Bcr-Abl residues with one escape mutation, T315I. The MADEAP sequence at the beginning has been added to the Bcr-Abl sequence for stability of yeast expression. The bolded and underlined text are mutations corresponding to escape mutant (T315I). The last 6 residues are a hexahistidine tag. The 328 amino acid sequence in between the MADEAP sequence and the hexahistidine tag are from the human Abl kinase domain. The final amino acid is a stop codon (*).

Construct #5 Fully Human Bcr-Abl WT Seq Containing Junction

```
                                                    (SEQ ID NO: 5)
MADEAPCFRSFSLTSVELQMLTNSCVKLQTVHSIPLTINKEDDESPGLYG       50

FLHVIVHSATGFKQSSKALQRPVASDFEPQGLSEAARWNSKENLLAGPSE      100

NDPNLFVALYDFVASGDNTLSITKGEKLRVLGYNHNGEWCEAQTKNGQGW      150

VPSNYITPVNSLEKHSWYHGPVSRNAAEYLLSSGINGSFLVRESESSPGQ      200

RSISLRYEGRVYHYRINTASDGKLYVSSESRFNTLAELVHHHSTVADGLI      250

TTLHYPAPKRNKPTVYGVSPNYDKWEMERTDITMKHKLGGGQYGEVYEGV      300

WKKYSLTVAVKTLKEDTMEVEEFLKEAAVMKEIKHPNLVQLLGVCTREPP      350

FYIITEFMTYGNLLDYLRECNRQEVNAVVLLYMATQISSAMEYLEKKNFI      400

HRDLAARNCLVGENHLVKVADFGLSRLMTGDHHHHHH*
```

This construct is the wild type human Bcr-Abl sequence containing the junction of Bcr and Abl. The MADEAP sequence at the beginning has been added to the Bcr-Abl sequence for stability of yeast expression. The last 6 residues are a hexahistidine tag. The sequence in between the MADEAP sequence and the hexahistidine tag are from human Bcr-Abl sequence containing 97 residues upstream of Bcr-Abl junction. The final amino acid is a stop codon (*).

Construct #6 Fully Human E1.E2.E3

```
                                                    (SEQ ID NO: 6)
MADEAPNLFVALYDFVASGDNTLSITKGEKLRVLGYNHNGEWCEAQTKNG       50

QGWVPSNYITPVNSLEKHSWYHGPVSRNAAEYLLSSGINGSFLVRESESS      100

PGQRSISLRYEGRVYHYRINTASDGKLYVSSESRFNTLAELVHHHSTVAD      150

GLITTLHYPAPKRNKPTVYGVSPNYDKWEMERTDITMKHKLGGGQYGKVY      200

EGVWKKYSLTVAVKTLKEDTMEVEEFLKEAAVMKEIKHPNLVQLLGVCTR      250

EPPFYIIIEFMTYGNLLDYLRECNRQEVNAVVLLYMATQISSATEYLEKK      300

NFIHRDLAARNCLVGENHLVKVADFGLSRLMTGDHHHHHH*
```

This construct contains three escape mutants: E255K, T315I, and M351T. The MADEAP sequence at the beginning has been added to the Bcr-Abl sequence for stability of yeast expression. The bolded and underlined text shows mutations corresponding to escape mutants (E255K, T315I, and M351T). The last 6 residues are a hexahistidine tag. The 328 amino acids in between the MADEAP sequence and the hexahistidine tag are from the human Abl kinase domain. The final amino acid is a stop codon (*).

Example 2

Mouse Model of Leukemia

The mouse model of leukemia was used whereby mice were injected with a retrovirus containing various forms of Bcr-Abl. These leukemic cells were engineered to express the green fluorescent protein (GFP), a marker for purposes of monitoring.

The mice were immunized 3 times at two week intervals with 2 YU yeast (20 million yeast). Challenge was with 500,000 leukemia cells on day 7 post-last vaccination. The mouse studies were divided into two parts:

There were 2 groups of mice in experiment #1:

(1) The first group was not immunized but challenged with GFP-labeled wild-type CML (Bcr-Abl but no escape mutations) (5 animals). (2) The second group of mice were immunized with a yeast-based vaccine containing Abl protein harboring three escape mutations found with Gleevec treatment (Bcr-Abl with 3 TAME epitopes—E255K, T315I, M351T, aka GI-10,001) and then challenged with GFP-labeled wild-type CML (Bcr-Abl but no TAME mutations) (5 animals)

The results were as follows:

FIG. 1 show the Kaplan-Meier curves, which were identical for these groups—all mice succumbed within the same 24 hour period on day 10. The vaccinated mice had elevated numbers of T and B cells in their spleen as well confirming the administration of the yeast-based vaccine and indicating a general innate immune activation to the administered vaccine.

There were 3 groups of mice in part 2 of the mouse studies:

(1) The first group was not immunized but challenged with GFP-labeled T315I CML (Bcr-Abl with 1 TAME mutation—T315I) (5 animals).

(2) The second group of mice was immunized with a yeast-based vaccine containing Abl protein harboring three escape mutations (Bcr-Abl with 3 TAME epitopes—E255K, T315I, M351T), and then challenged with GFP-labeled T315I CML (Bcr-Abl with 1 TAME mutation—T315I) (3 animals)

(3) The third group of mice were immunized with a yeast-based vaccine containing Abl protein with one escape mutation (Bcr-Abl with 1 TAME epitope—T315I), and then challenged with GFP-labeled T315I CML (Bcr-Abl with 1 TAME mutation—T315I) (4 animals)

Figure 2:
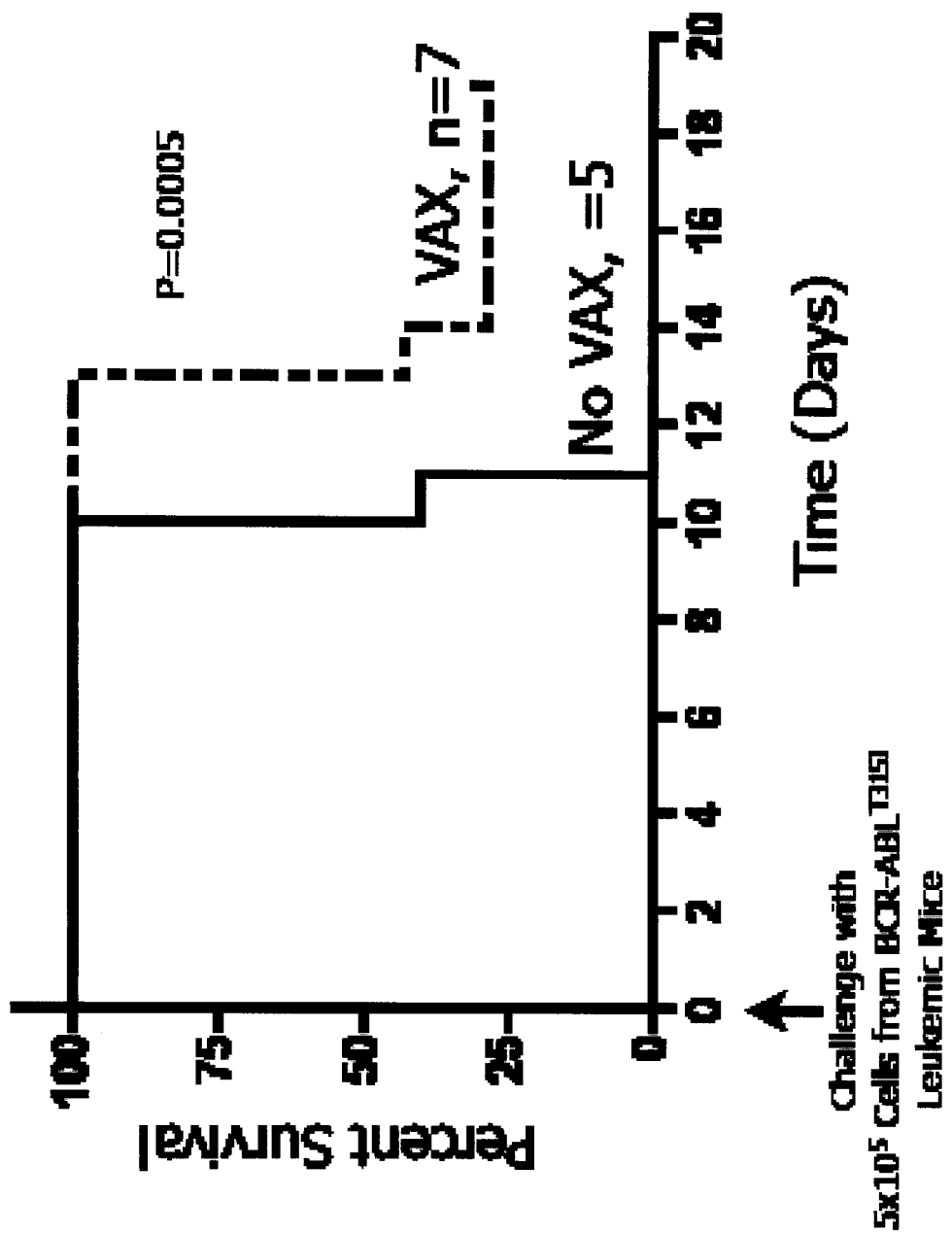
FIG. 2 depicts a survival curve against mutated leukemia for control vs. vaccinated mice.

The results are as follows:

FIG. 2 depicts the Kaplan-Meier curves, which showed a clear survival advantage for the vaccinated mice. In the control groups (group #1), all the mice died within a 24 hour period on days 10-11 (5/5 dead). In contrast, the vaccinated group of mice all survived past day 11. There were no dead mice of a total of 7 mice in the vaccinated group as of day 13, and two mice survived at least past day 35.

Figure 3:
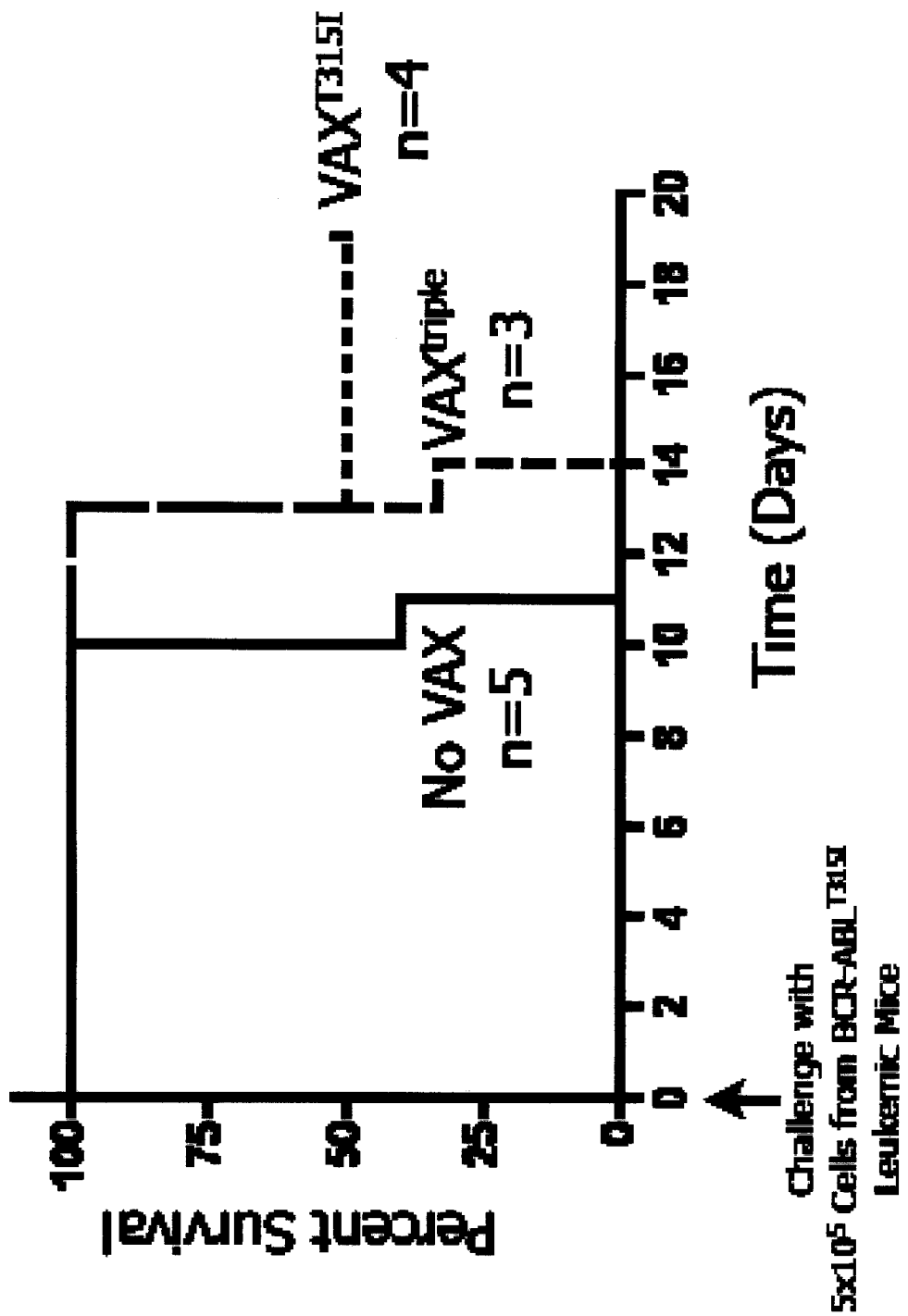
FIG. 3 depicts a survival curve for mice immunized with two different Tarmogen constructs: GI-10,001 (Tarmogen containing three escape mutations (E255K, T315I and M351T)) and GI-10,002 (Tarmogen containing one escape mutation (T315I)).

FIG. 3 depicts the Kaplan-Meier curves for the same group of mice with the vaccinated mice further delineated into those which received the vaccine with the three escape mutations (GI-10,001) and those which received the vaccine with the T315I mutation.

From FIGS. 1-2, it is readily apparent that the targeted ablation methodology targets the cells with the escape mutation(s) and not wild type Bcr-Abl. As such, it provides a very useful tool for immune recognition of leukemic cells that have escaped in the face of existing cancer therapeutic agents. FIGS. 2 and 3 show that either type of vaccine will be effective to target the destruction of cells that express the escape mutation. The use of either vaccine can be used to prolong the survival of the mice that have been challenged with the leukemic cells. The use of a multi-mutation cassette or a single mutation cassette can be used to target cells expression escape mutation(s).

Figure 4:
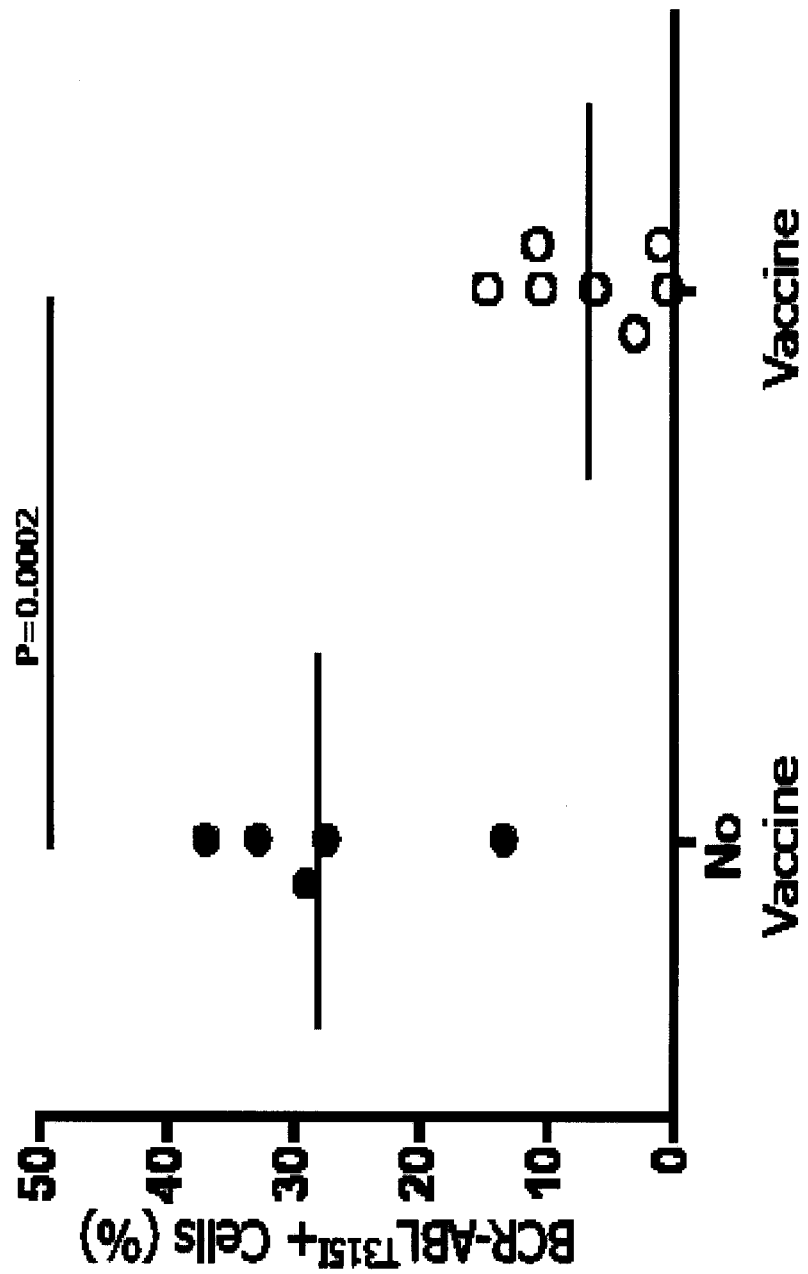
FIG. 4 depicts the leukemic cell counts in the control vs. vaccinated mice. The mice were vaccinated with Tarmogen containing the T315I escape mutation. The y-axis indicates the percentage of GFP-positive cells. The two open circles near 0 indicate vaccinated mice that show very little leukemic cell burden.

When the percentage of leukemic cells was measured in the second part of the experiment, the vaccinated mice had statistically significant decrease in the percentage of leukemic cells in their blood on day 10 as compared to non-vaccinated mice. These results are shown in FIG. 4. The two open dots near the 0 mark indicate mice with very little to no detectable leukemic cell burden.

Figure 5:
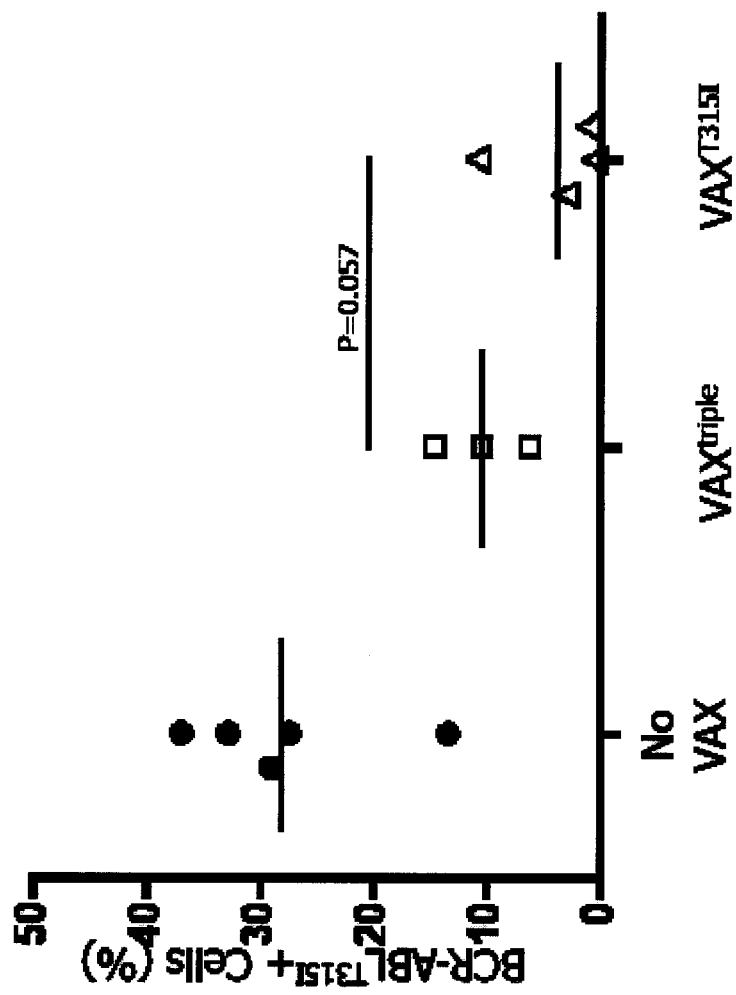
FIG. 5 depicts leukemic cell counts in mice which have received either no vaccination, vaccination with GI-10,001 (Tarmogen containing three escape mutations (E255K, T315I and M351T)) or GI-10,002 (Tarmogen containing one escape mutation (T315I)).

FIG. 5 show the leukemic burden as distributed by the different vaccines. Both GI-10,001 (triple mutation) and GI-10,002 (T315I mutation) are effective to target the immune cells that express the escape mutation.

What is claimed is:

1. A method for targeting the ablation of a mutational escape in an individual with cancer, wherein the cancer comprises Bcr-Abl or Bcr-Abl comprising T315I, E255K and/or M351T mutations, comprising administering to the individual in conjunction with an effective amount of imatinib a composition comprising a yeast vehicle transformed with a nucleic acid which encodes a polypeptide comprising a Bcr-Abl sequence of SEQ ID NO:4 or SEQ ID NO:6.

2. The method of claim 1, wherein the yeast vehicle is from yeast selected from the group consisting of *Saccharomyces, Schizosaccharomyces, Kluveromyces, Hansenula, Candida* and *Pichia*.

3. The method of claim 1, wherein the yeast vehicle is from *Saccharomyces*.

4. The method of claim 1, wherein the yeast vehicle is from *Saccharomyces cerevisiae*.

5. The method of claim 1, wherein the yeast vehicle is a whole yeast.

6. The method of claim 5, wherein whole yeast is heat-killed.

7. The method of claim 1, wherein the yeast vehicle is lyophilized prior to administration.

8. The method of claim 1, wherein the composition is formulated for injection.

9. The method of claim 1, wherein the composition is administered separately from administration of imatinib.

10. The method of claim 1, wherein the composition is administered prior to or after the administration of imatinib.

11. The method of claim 1, further comprising administering boosters of the composition weekly or monthly.

12. The method of claim 1, wherein the cancer is a leukemia.

13. A method for targeting the ablation of a mutational escape in an individual with cancer, wherein the cancer comprises Bcr-Abl, comprising administering to the individual in conjunction with an effective amount of imatinib a composition comprising a yeast vehicle transformed with a nucleic acid which encodes a polypeptide comprising a Bcr-Abl junction sequence of SEQ ID NO:5.

14. The method of claim 13, wherein the yeast vehicle is from *Saccharomyces cerevisiae*.

15. The method of claim 13, wherein the yeast vehicle is a whole yeast.

16. The method of claim 15, wherein whole yeast is heat-killed.

17. The method of claim 13, wherein the composition is formulated for injection.

18. The method of claim 13, wherein the composition is administered separately from administration of imatinib.

19. The method of claim 13, wherein the composition is administered prior to or after the administration of imatinib.

20. The method of claim 13, wherein the cancer is a leukemia.

* * * * *